(12) United States Patent
Sayers et al.

(10) Patent No.: US 12,018,045 B2
(45) Date of Patent: Jun. 25, 2024

(54) 17-BETA-HYDROXYWITHANOLIDES AND USE THEREOF IN TREATING CANCER

(71) Applicants: The United States of America, as represented by the Secretary, Department of Health and Human Services, Bethesda, MD (US); Arizona Board of Regents on Behalf of the University of Arizona, Tucson, AZ (US)

(72) Inventors: Thomas J. Sayers, Boonsboro, MD (US); Poonam Tewary, Frederick, MD (US); Leslie Gunatilaka, Tucson, AZ (US); Alan D. Brooks, Frederick, MD (US); Kithsiri Wijeratne, Tucson, AZ (US); Yaming Xu, Tucson, AZ (US)

(73) Assignees: The United States of America, as represented by the Secretary, Department of Health and Human Services, Bethesda, MD (US); Arizona Board of Regents on Behalf of the University of Arizona, Tucson, AZ (US)

( * ) Notice: Subject to any disclaimer, the term of this patent is extended or adjusted under 35 U.S.C. 154(b) by 382 days.

(21) Appl. No.: 16/978,442

(22) PCT Filed: Mar. 6, 2019

(86) PCT No.: PCT/US2019/020989
§ 371 (c)(1),
(2) Date: Sep. 4, 2020

(87) PCT Pub. No.: WO2019/173499
PCT Pub. Date: Sep. 12, 2019

(65) Prior Publication Data
US 2021/0047363 A1 Feb. 18, 2021

Related U.S. Application Data

(60) Provisional application No. 62/639,337, filed on Mar. 6, 2018.

(51) Int. Cl.
*A61K 45/06* (2006.01)
*C07J 71/00* (2006.01)

(52) U.S. Cl.
CPC ............. *C07J 71/001* (2013.01); *A61K 45/06* (2013.01)

(58) Field of Classification Search
CPC ...... C07J 71/001; A61K 45/06; A61K 31/404; A61K 31/58; A61K 31/635
See application file for complete search history.

(56) References Cited

U.S. PATENT DOCUMENTS

| 4,235,871 A | 11/1980 | Papahadjopoulos et al. |
| 4,501,728 A | 2/1985 | Geho et al. |
| (Continued) | | |

FOREIGN PATENT DOCUMENTS

| WO | WO 98/51793 A1 | 11/1998 |
| WO | WO 2006/017961 A1 | 2/2006 |
| (Continued) | | |

OTHER PUBLICATIONS

Deluca et al., "Parenteral Drug-Delivery Systems," *Pharmaceutics and Pharmacy Practice*, Chapter 8, J.B. Lippincott Company, Philadelphia, PA, pp. 238-250 (1982).
(Continued)

*Primary Examiner* — Clinton A Brooks
*Assistant Examiner* — Andrew P Lee
(74) *Attorney, Agent, or Firm* — Leydig, Voit & Mayer, Ltd.

(57) ABSTRACT

Disclosed are compounds suitable for enhancing cancer treatment, for example, a compound of formula (I): (I)
(Continued)

wherein $R^1$ is as defined herein. Also disclosed is a method of enhancing the response of cancer cells in a mammal to treatment with an apoptosis inducing ligand, a method of inducing apoptosis in cancer cells in a mammal, and a method of treating prostate cancer in mammal in need thereof comprising administration of a compound described herein.

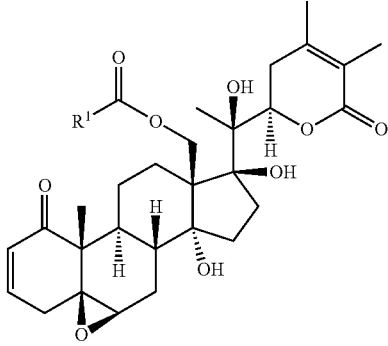

(I)

10 Claims, 24 Drawing Sheets

(56) References Cited

U.S. PATENT DOCUMENTS

| 4,837,028 | A | 6/1989 | Allen |
|---|---|---|---|
| 5,019,369 | A | 5/1991 | Presant et al. |
| 7,244,429 | B2 | 7/2007 | Zhou et al. |
| 9,238,069 | B2 | 1/2016 | Sayers et al. |
| 2002/0004227 | A1 | 1/2002 | Ashkenazi et al. |
| 2004/0214235 | A1 | 10/2004 | Mori et al. |
| 2005/0079172 | A1 | 4/2005 | Nasoff et al. |
| 2006/0269554 | A1 | 11/2006 | Adams |
| 2006/0269555 | A1 | 11/2006 | Salcedo et al. |
| 2006/0270837 | A1 | 11/2006 | Salcedo et al. |
| 2007/0179086 | A1 | 8/2007 | Gliniak et al. |
| 2007/0292411 | A1 | 12/2007 | Salcedo et al. |
| 2007/0298039 | A1 | 12/2007 | Zhou et al. |
| 2019/0046543 | A1* | 2/2019 | Sayers .............. C07J 17/00 |

FOREIGN PATENT DOCUMENTS

| WO | WO 2017/087857 A1 | 5/2017 |
|---|---|---|
| WO | WO 2017/139485 A1 | 8/2017 |

OTHER PUBLICATIONS

Estornes et al., "dsRNA induces apoptosis through an atypical death complex associating TLR3 to caspase-8," *Cell Death and Differentiation*, 19:1482-1494 (2012).
Gay et al., "Toll-like receptors as molecular switches," *Nature Reviews—Immunology*, 6:693-698 (2006).
International Bureau of WIPO, International Preliminary Report on Patentability in International Patent Application No. PCT/US2019/020989, dated Sep. 17, 2020 (9 pp.).
International Searching Authority, International Search Report in International Patent Application No. PCT/US2019/020989, dated Jul. 5, 2019 (6 pp.).
International Searching Authority, Written Opinion in International Patent Application No. PCT/US2019/020989, dated Jul. 5, 2019 (7 pp.).
Salaun et al., "TLR3 Can Directly Trigger Apoptosis in Human Cancer Cells," *The Journal of Immunolog*, 176:4894-4901 (2006).
Salaun et al., "Toll-like Receptor 3 Expressed by Melanoma Cells as a Target for Therapy?" *Clin Cancer Res*, 13(15): 4565-4574 (Aug. 1, 2007).
Scudiero et al., "Evaluation of a Soluble Tetrazolium/Formazan Assay for Cell Growth and Drug Sensitivity in Culture Using Human and Other Tumor Cell Lines," *Cancer Research*, 48:4827-4833 (1988).
Skehan et al., "New Colorimetric Cytotoxicity Assay for Anticancer-Drug Screening," *J. Nat. Cancer Inst.*, 82:1107-1112 (1990).
Szoka, Jr. et al., "Comparative Properties and Methods of Preparation of Lipid Vesicles (Liposomes)," *Annual Review of Biophysics & Bioengineering*, 9:467-508 (1980).
Trissel, "Intravenous Infusion Solutions," *ASHP Handbook on Injectable Drugs*, Fourth Edition, American Society of Hospital Pharmacists, Inc., Bethesda, MD, pp. 622-630 (1986).

* cited by examiner

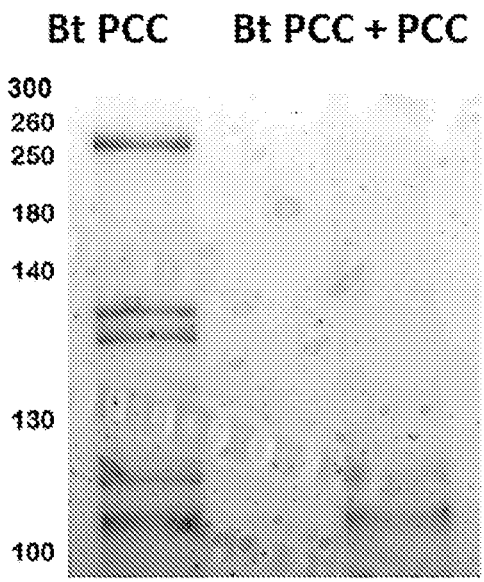
FIG. 19A
| Identification of proteins using Mass Spectrometry (# Peptide Spectrum Matches) | | | |
|---|---|---|---|
| PAGE Gel Band | 1 | 2 | 3 |
| Bromodomain-containing protein 4 UniProt O60885 | 822 | 54 | 123 |
| Bromodomain-containing protein 4 UniProt P25440 | | 384 | 112 |
| Bromodomain-containing protein 4 UniProt Q15059 | | 15 | 165 |
FIG. 19B
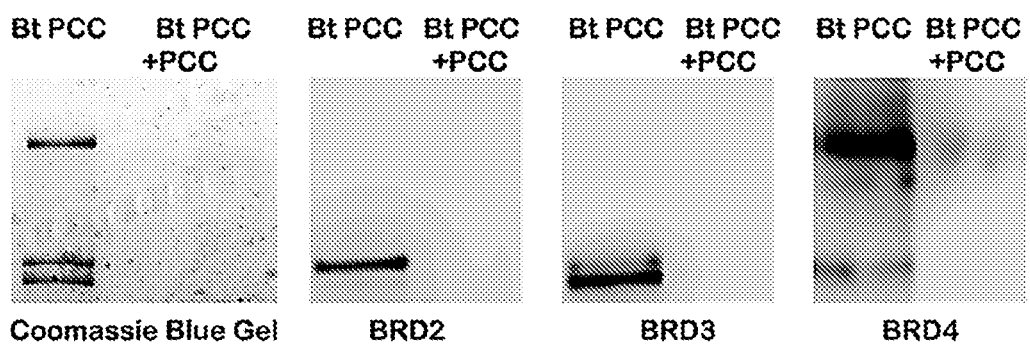
FIG. 19C

17-BETA-HYDROXYWITHANOLIDES AND USE THEREOF IN TREATING CANCER

CROSS REFERENCE TO A RELATED APPLICATION

This patent application is the U.S. national stage of International Patent Application No. PCT/US2019/020989, filed Mar. 6, 2019, which claims the benefit of U.S. Provisional Patent Application No. 62/639,337 filed Mar. 6, 2018, the disclosures of which are incorporated herein by reference in their entireties for all purposes.

STATEMENT REGARDING FEDERALLY SPONSORED RESEARCH OR DEVELOPMENT

This invention was made with government support under Grant No. HHSN261200800001E awarded by National Institutes of Health. The government has certain rights in this invention.

BACKGROUND OF THE INVENTION

One strategy in developing new cancer therapeutics having better toxicity profiles compared with current cytotoxic drugs is to utilize molecularly-targeted therapeutics that selectively target cancer cells versus normal cells. Such molecularly-targeted therapeutics can be used in minimal doses to reduce side effects. Death receptor ligands held initial promise in answering this need because they trigger programmed cell death in their target cancer cells. Two of the best-studied death receptor ligands, Fas ligand and tumor necrosis factor-alpha (TNF-α), have proven to be too toxic for systemic use as anticancer agents in their native forms. However, another death receptor ligand, tumor necrosis factor-α-related apoptosis-inducing ligand, known as TRAIL, and its receptors, has renewed interest in this area of cancer research. Active TRAIL receptors, TR1 (DR4) and TR2 (DR5) are often more highly expressed on cancer cells versus normal cells. Inactive TRAIL "decoy" receptors TR3 (DcR1) and TR4 (DcR2) are sometimes more prevalent on the surface of normal cells. Both DR4 and DR5 transduce death signaling, leading to apoptosis upon binding to TRAIL. Instead, DcR1 and DcR2 lack intact intracellular death domain and therefore cannot signal apoptosis despite binding to TRAIL. Instead, DcR1 or DcR2 protects cells from TRAIL-induced apoptosis by competing with DR4 and DR5 for binding to TRAIL. Interestingly, the expression of DcR1 and DcR2 is either downregulated or lost in many types of cancer cells or tissues while DR4 and DR5 expressions are maintained in cancer cells or tissues. This inversely related expression pattern for TRAIL receptors may be partly responsible for the selectivity of TRAIL ligand for tumor cells over normal cells, and its ability to preferentially cause apoptotic cell death in cancer cells, which may also contribute to a more favorable safety profile.

While TRAIL has been reported to successfully target certain tumor cells which are resistant to traditional chemotherapies or radiation, TRAIL resistance has also been widely documented. Many cancer cells are quite resistant to TRAIL as a single agent. Recently it was reported that signaling via Toll-like Receptor (TLR) ligands, particularly TLR3, could also promote apoptosis in certain cancer cells. However, this apoptosis signaling in most cancer cells was relatively weak, and was only significant following longer term incubations of 48-72 h with the RNA double-stranded TLR-3 ligand poly IC (Salaun et al., *J. Immunol.*, 2006, 176: 4894-4901; Salaun et al., *Clin. Cancer Res.*, 2007, 13: 4565-4574)). Nonetheless, some of the same molecular components of the apoptosis signaling pathway are thought to be engaged downstream of both death receptor and TLR ligand signaling (Estornes et al., *Cell Death. Differ.*, 2012, 19: 1482-1494; Weber et al., *Cell Death. Differ.*, 2010, 17: 942-951). However, TLR ligands such as poly (I:C) are also potent adjuvants for enhancing anti-cancer immune responses (Gay et al., *Nat. Rev. Immunol.*, 2006, 6: 693-698).

Thus, there is an unmet need for the development of sensitizers of the cancer cells to apoptosis inducing ligands such as poly (I:C) and TRAIL, especially those that act in a synergistic manner.

BRIEF SUMMARY OF THE INVENTION

The invention provides a compound of formula (I):

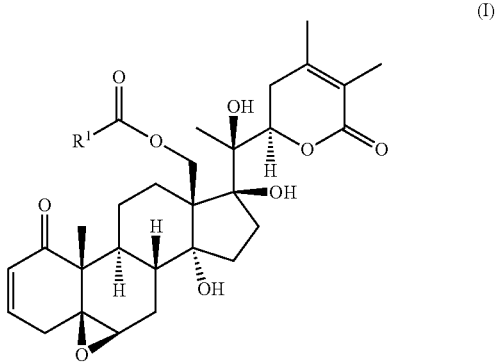

wherein $R^1$ is $C_2$-$C_{10}$ alkyl, $C_3$-$C_8$ cycloalkyl, $C_6$-$C_{10}$ aryl, $C_6$-$C_{10}$ aryl-$C_1$-$C_{10}$ alkyl, $C_6$-$C_{10}$ aryl-$C_2$-$C_{10}$ alkenyl, monocyclic heteroaryl, bicyclic heteroaryl, monocyclic heteroaryl-$C_1$-$C_{10}$ alkyl, bicyclic heteroaryl-$C_1$-$C_{10}$ alkyl, or 4-alkylenyl-tetrahydro-1H-thieno[3,4-d]imidazol-2(3H)-one, wherein the aryl or heteroaryl portion of $R^1$ is optionally substituted with one or more substituents selected from the group consisting of alkyl, alkoxy, aryl, thioalkoxy, heterocyclyl, and nitro.

The invention also provides a compound selected from the group consisting of:

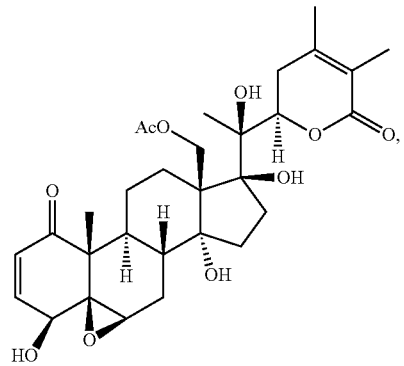

-continued

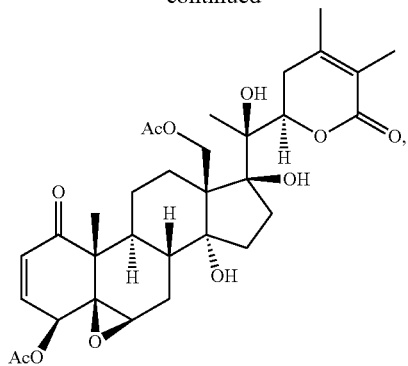

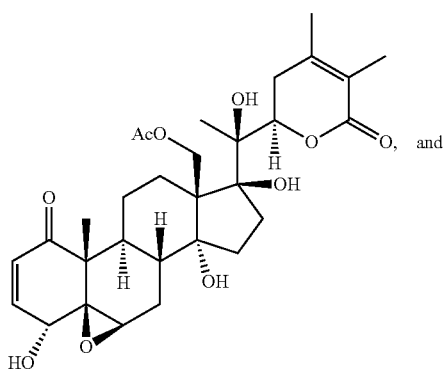

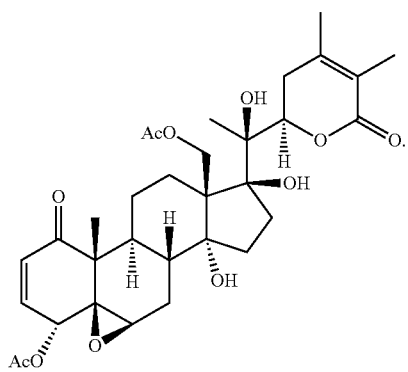

The invention further provides a method of synergistically enhancing the response of cancer cells in a mammal to treatment with an apoptosis-inducing ligand, which method comprises administering to the mammal an effective amount of a compound of the invention, and administering an effective amount of an apoptosis-inducing ligand, whereby a synergistic enhancement of the response is obtained.

The invention additionally provides a method of inducing apoptosis in cancer cells in a mammal that are resistant to treatment with an apoptosis-inducing ligand, which method comprises administering to the mammal an effective amount of a compound as described herein, and administering an effective amount of an apoptosis-inducing ligand, whereby a synergistic enhancement of the response is obtained.

The invention also provides a compound of formula (II):

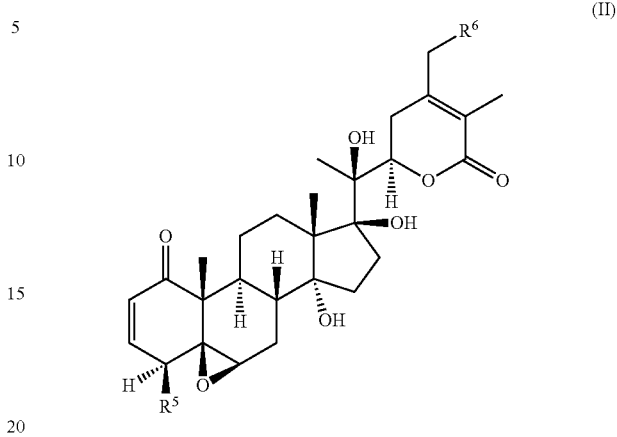

wherein $R^6$ is H and $R^5$ is

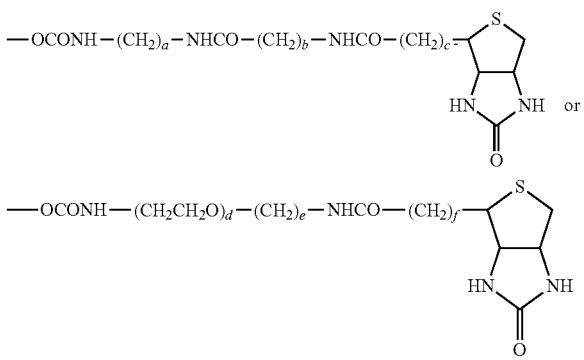

or wherein $R^5$ is H and $R^6$ is

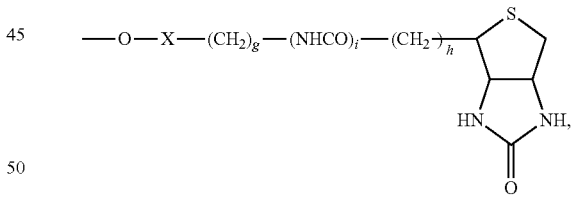

wherein a, b, c, d, e, and f are independently integers of from 1 to 10,

X is NH or absent, and wherein g and h are integers of from 1 to 5 and i is 0 or 1.

Desirably, the compounds of the invention sensitize cancer cells to apoptosis induced by apoptosis-inducing ligands, whether administered exogenously or produced in vivo by anti-cancer T cells administered as part of an immunotherapy regimen. The inventive compounds also desirably induce apoptosis in mammalian cancer cells that are resistant to treatment with an apoptosis-inducing ligand, thereby improving the response of an afflicted mammal to treatment with the apoptosis-inducing ligand.

BRIEF DESCRIPTION OF THE SEVERAL VIEWS OF THE DRAWING(S)

Figure 1:
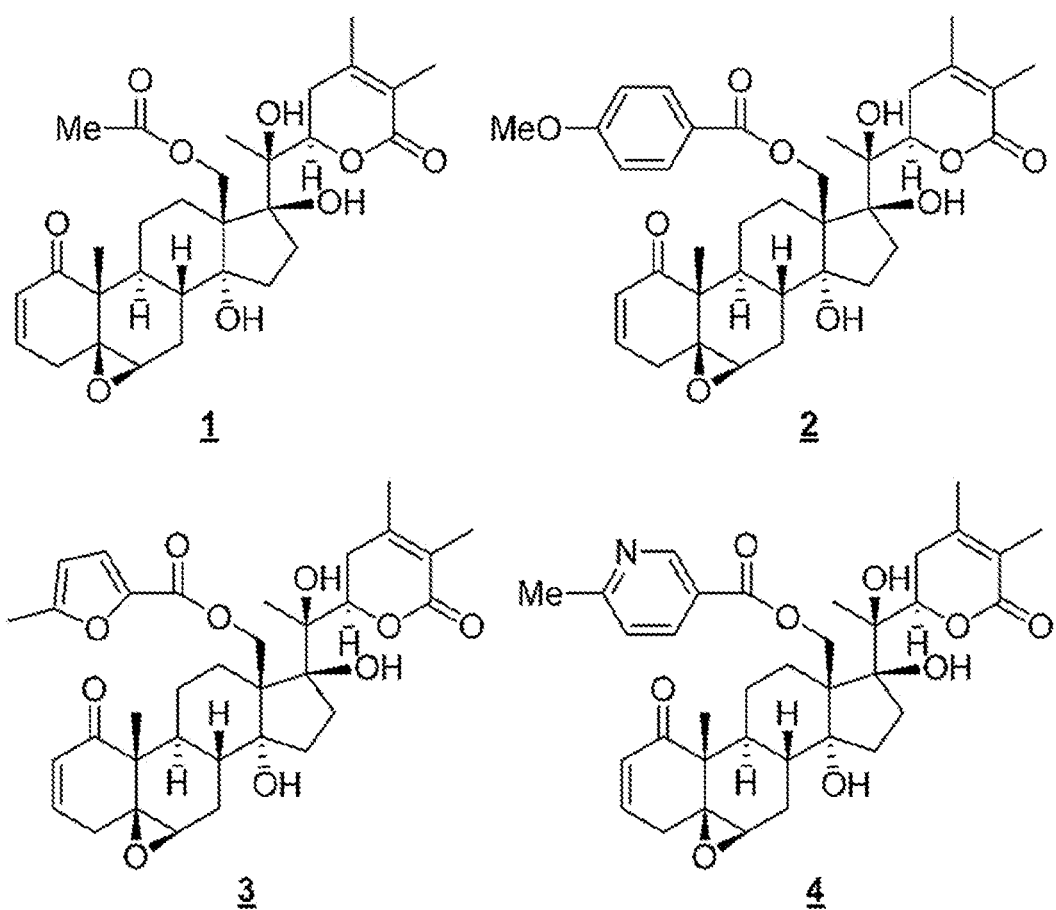
FIG. 1 depicts the structures of compounds 1-4, in accordance with embodiments of the invention.
Figure 2A:
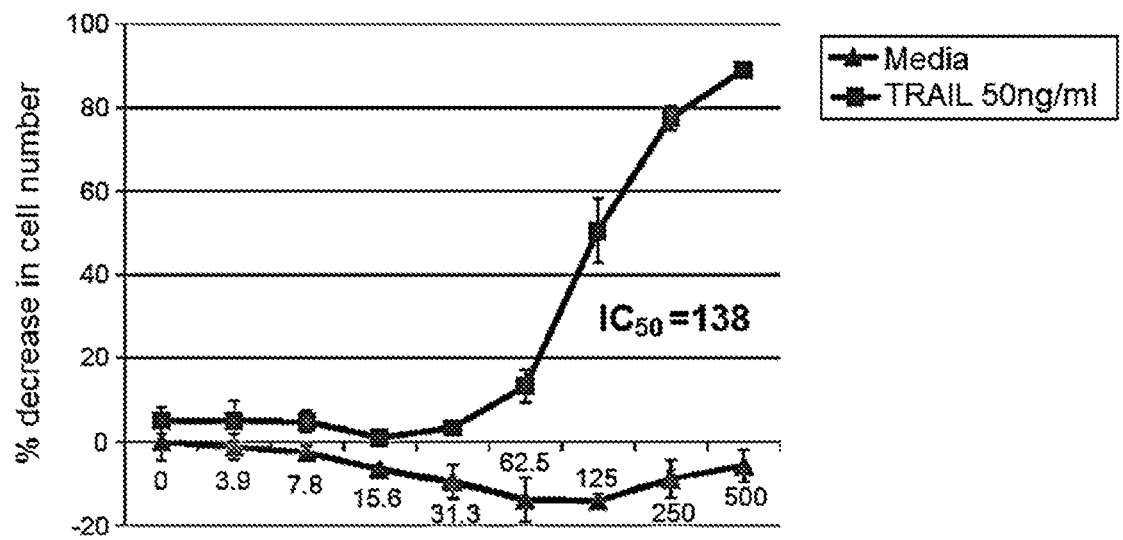
FIG. 2A depicts the results of titration experiments on the sensitization of human renal carcinoma cell line ACHN by compound 1 in the presence or absence of TRAIL.
Figure 2B:
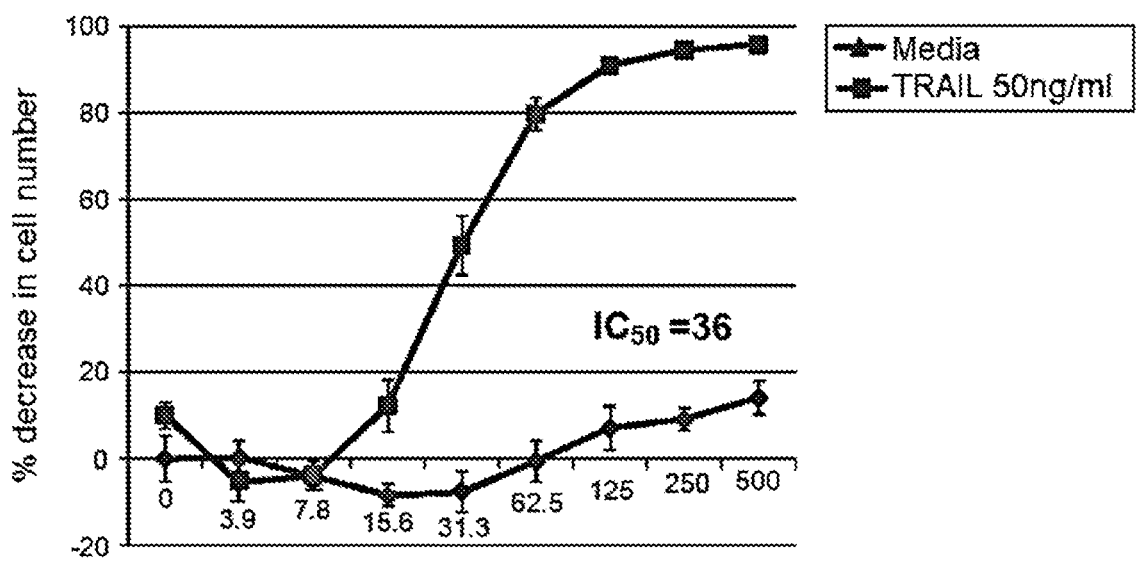
FIG. 2B depicts the results of titration experiments on the sensitization of renal carcinoma cell line ACHN by compound 2 in the presence or absence of TRAIL.
Figure 2C:
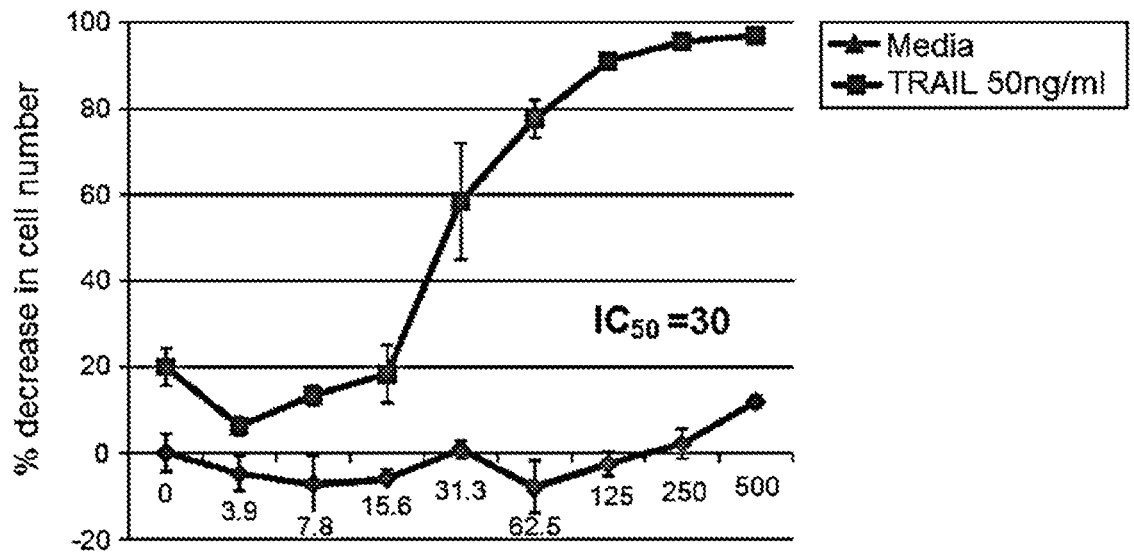
FIG. 2C depicts the results of titration experiments on the sensitization of renal carcinoma cell line ACHN by compound 3 in the presence or absence of TRAIL.
Figure 2D:
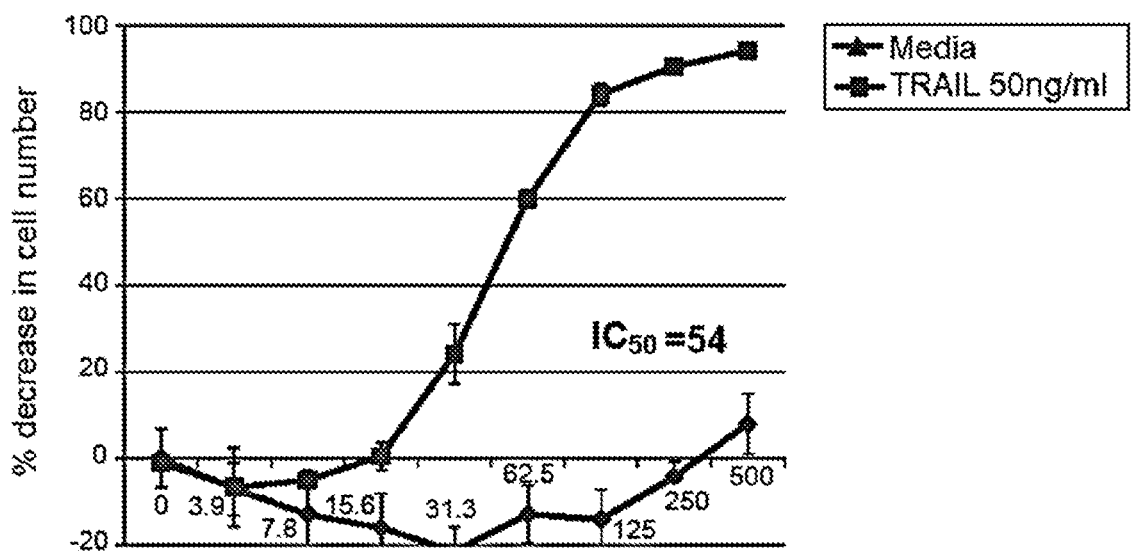
FIG. 2D depicts the results of titration experiments on the sensitization of renal carcinoma cell line ACHN by compound 4 in the presence or absence of TRAIL.
Figure 3:
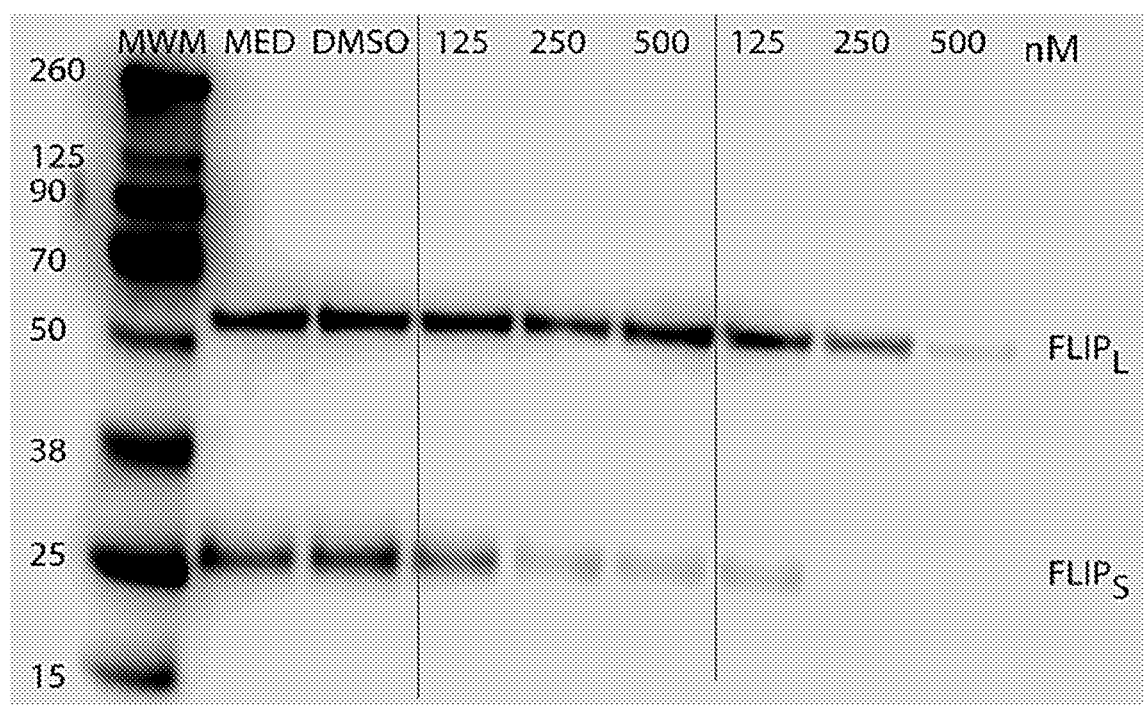

FIG. 3 shows the effect of compounds 1 and 3 on the reduction of cFLIP in ACHN human carcinoma cells as a function of concentration after 24 exposure to the compounds.

Figure 4:
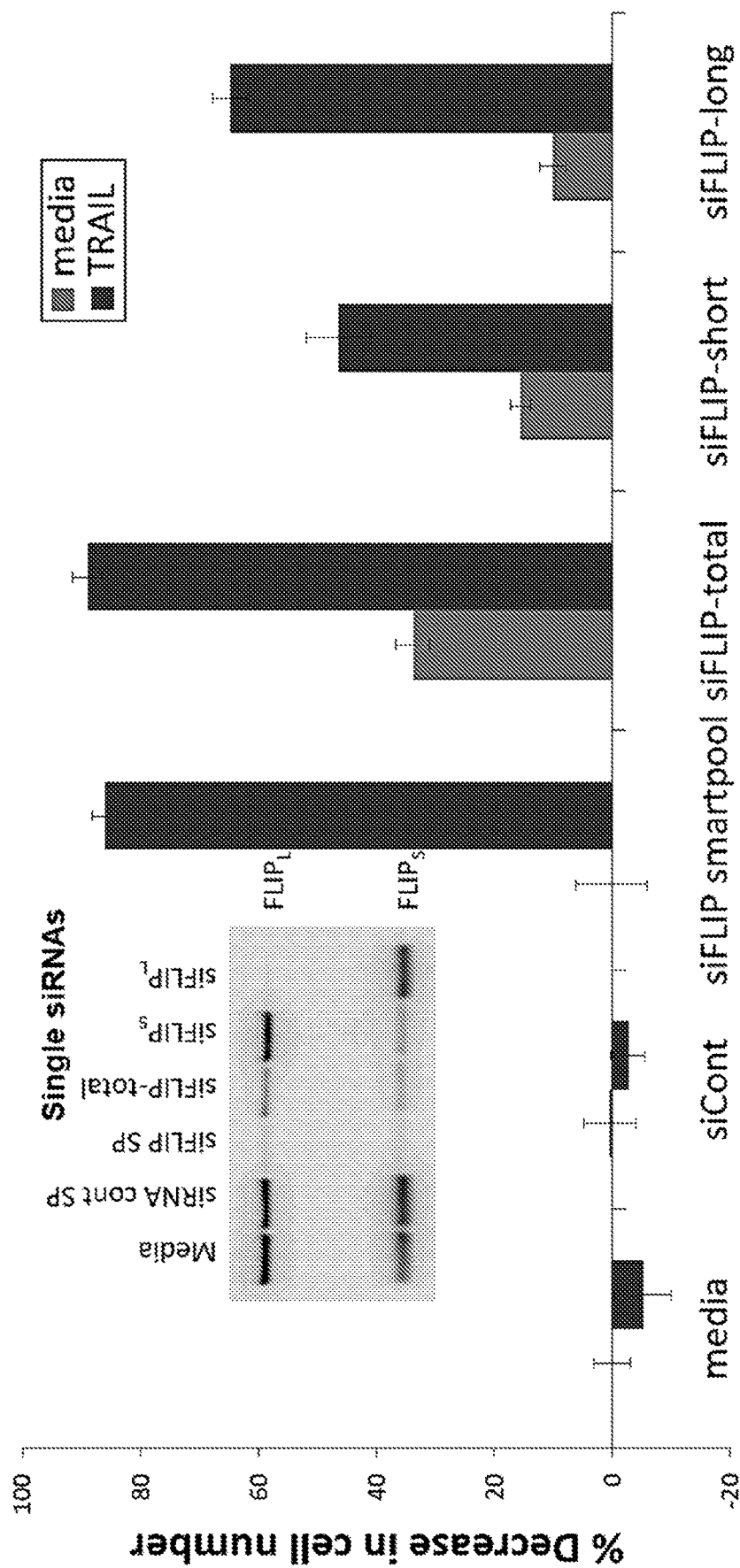

FIG. 4 shows the percentage decrease in cell number for ACN human renal carcinoma cells treated with media and with the siRNAs siCont, siFLIP smartpool, siFLIP-total, siFLIP-short, and siFLIP-long.

Figure 5A:
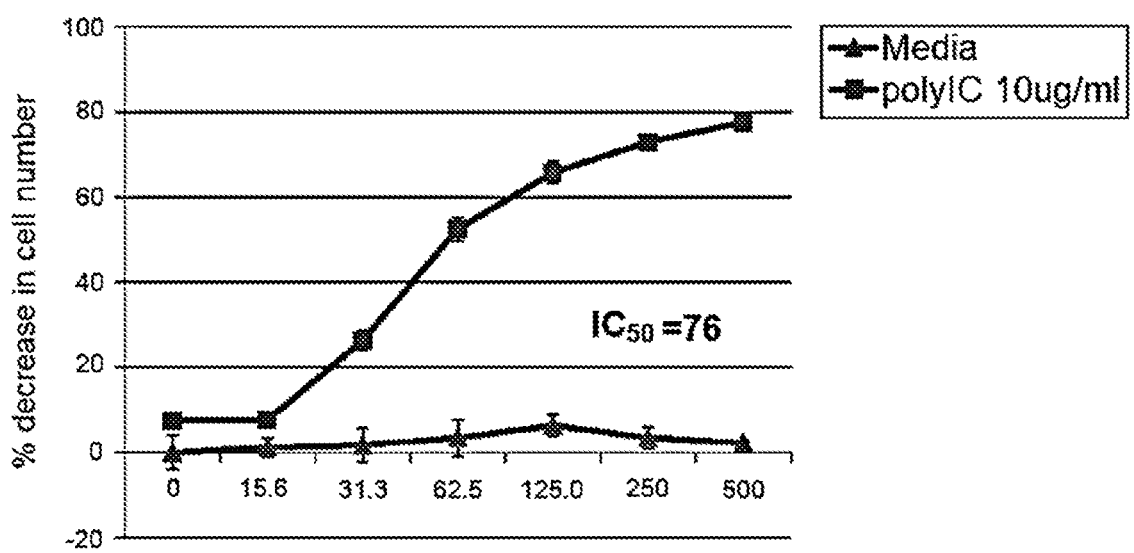

FIG. 5A depicts the results of titration experiments on the sensitization of SK-MEL-28 melanoma cells by compound 1 in the presence or absence of poly(I:C).

Figure 5B:
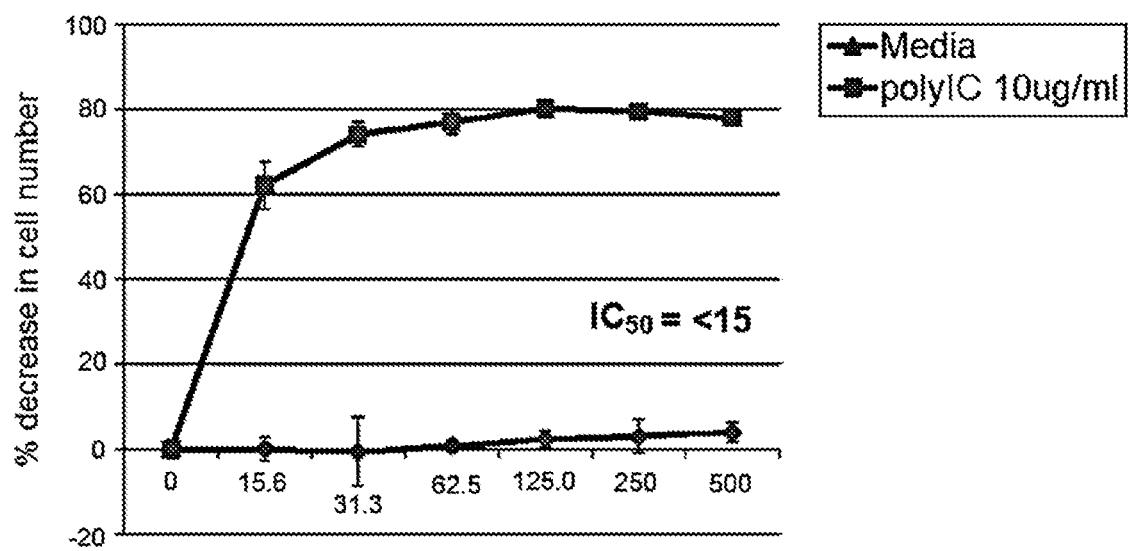

FIG. 5B depicts the results of titration experiments on the sensitization of SK-MEL-28 melanoma cells by compound 2 in the presence or absence of poly(I:C).

Figure 5C:
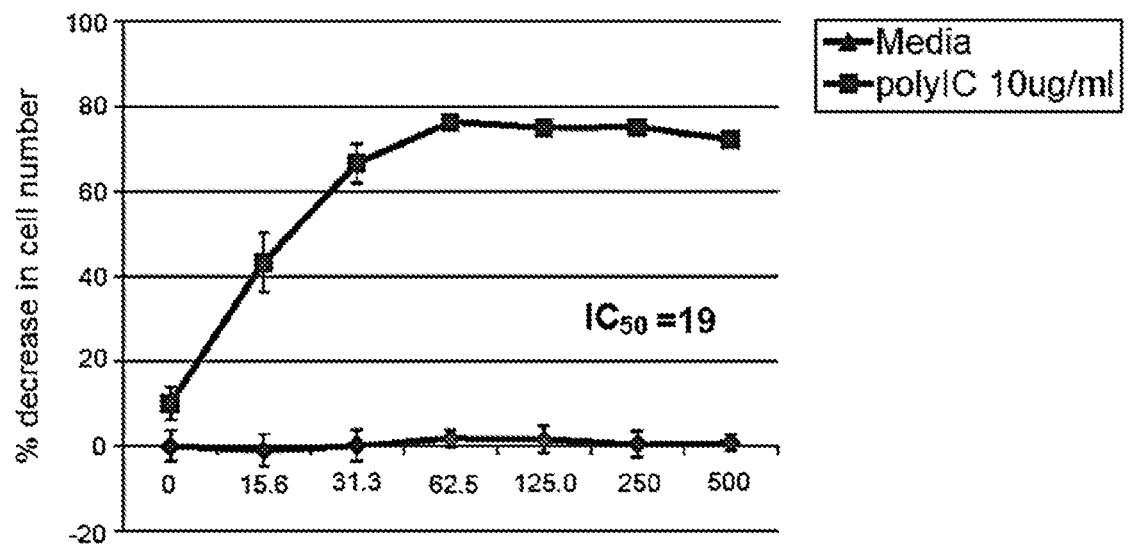

FIG. 5C depicts the results of titration experiments on the sensitization of SK-MEL-28 melanoma cells by compound 3 in the presence or absence of poly(I:C).

Figure 5D:
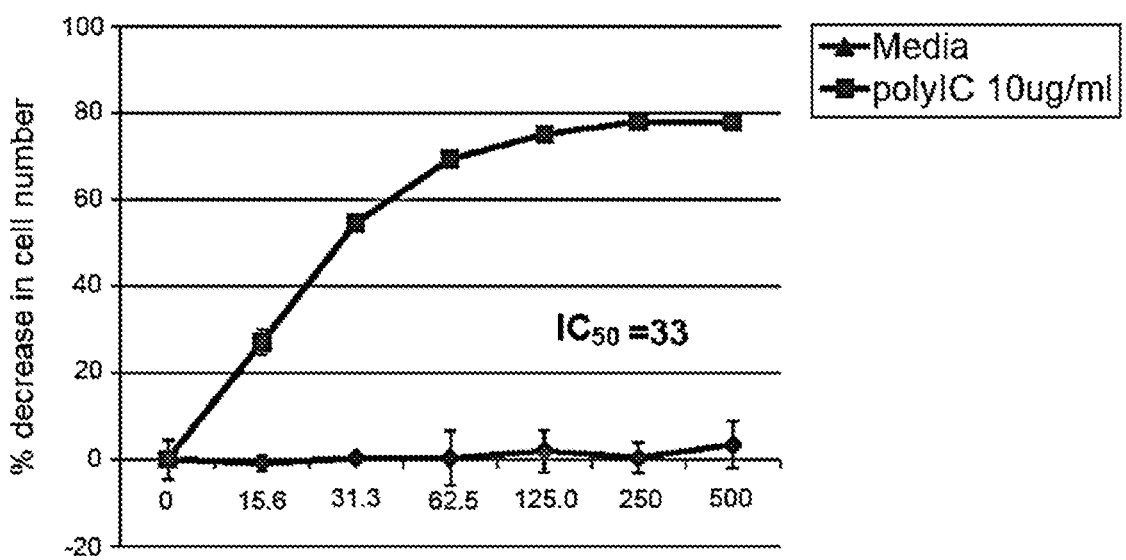

FIG. 5D depicts the results of titration experiments on the sensitization of SK-MEL-28 melanoma cells by compound 4 in the presence or absence of poly(I:C).

Figure 6:
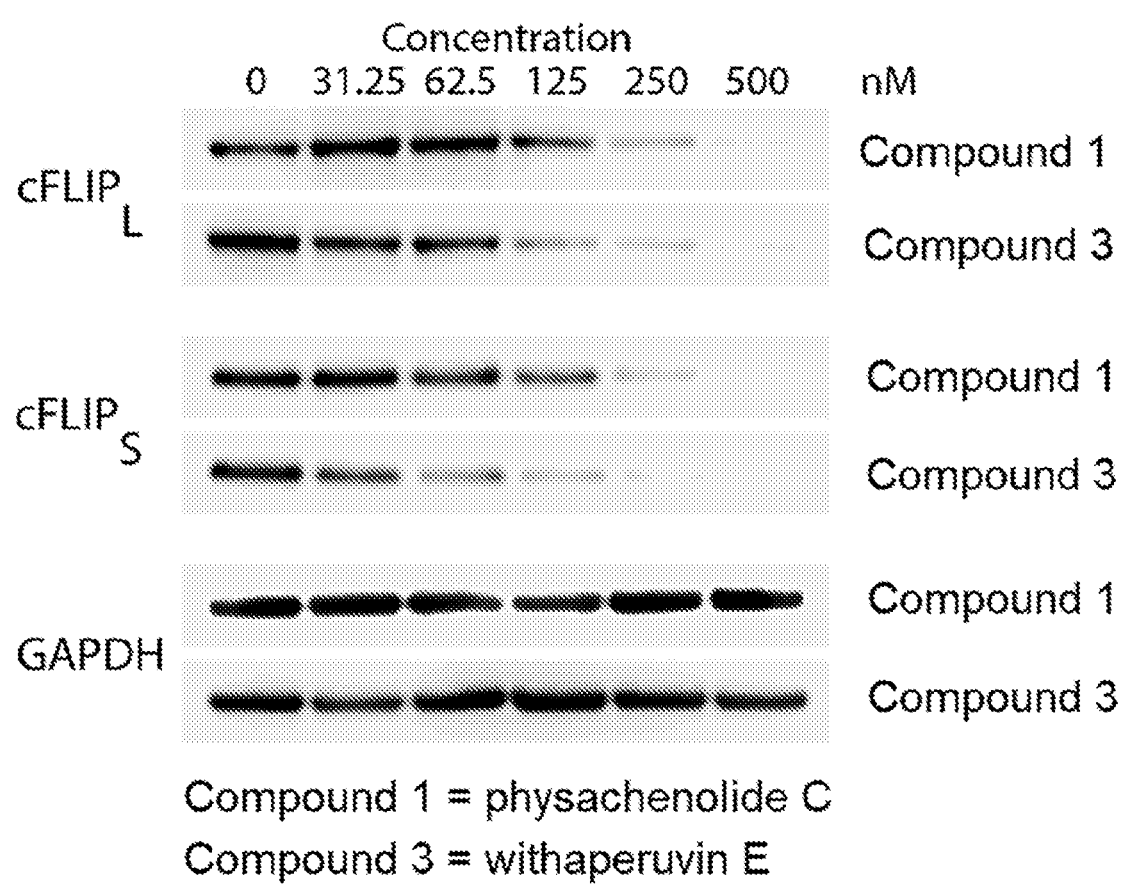

FIG. 6 shows the effect of compound 1 (physachenolide C) and 3 (withaperuvin E) on the reduction of $cFLIP_L$, $cFLIP_S$, and GAPDH in M14 human melanoma cells as a function of concentration.

Figure 7A:
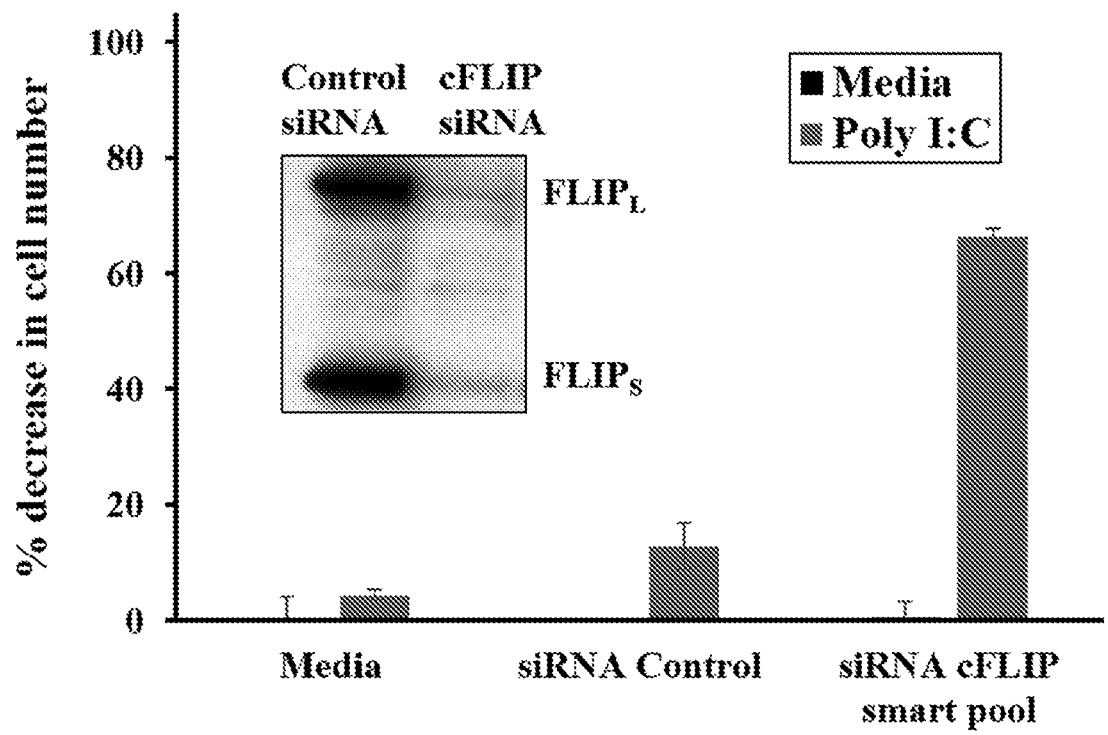

FIG. 7A shows the percentage decrease in cell numbers for SK-MEL-28 melanoma cells treated with media, siRNA control, and siRNA cFLIP smart pool in the presence and absence of poly (I:C).

Figure 7B:
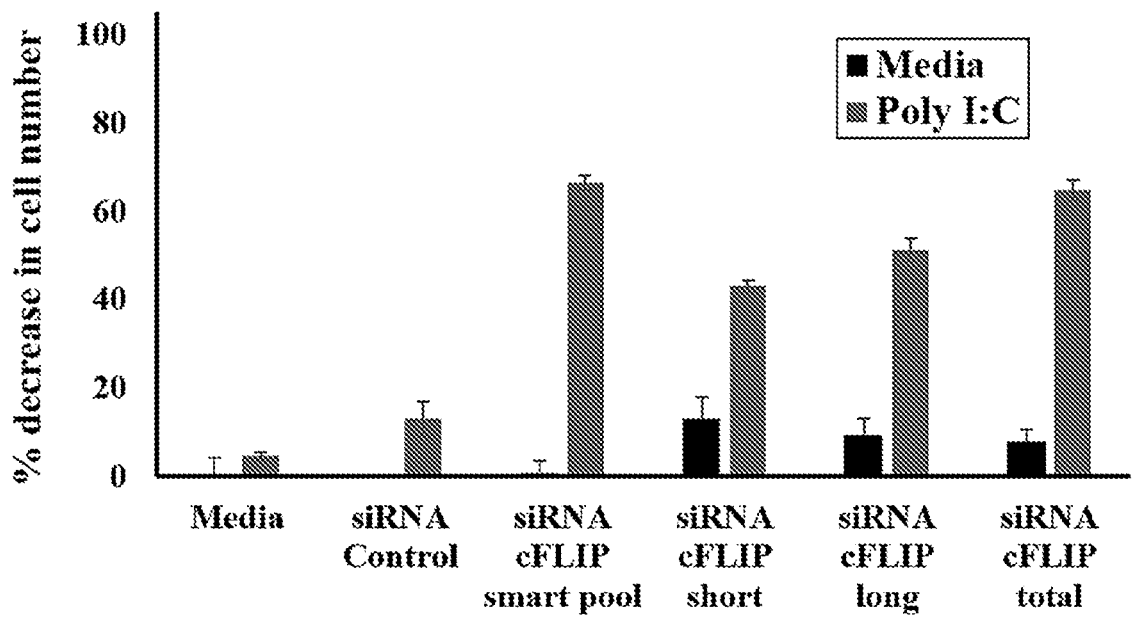

FIG. 7B shows the percentage decrease in cell numbers for SK-MEL-28 melanoma cells treated with media, siRNA control, siRNA cFLIP smart pool, siRNA cFLIP short, siRNA cFLIP long, and siRNA cFLIP total in the presence and absence of poly (I:C).

Figure 8A:
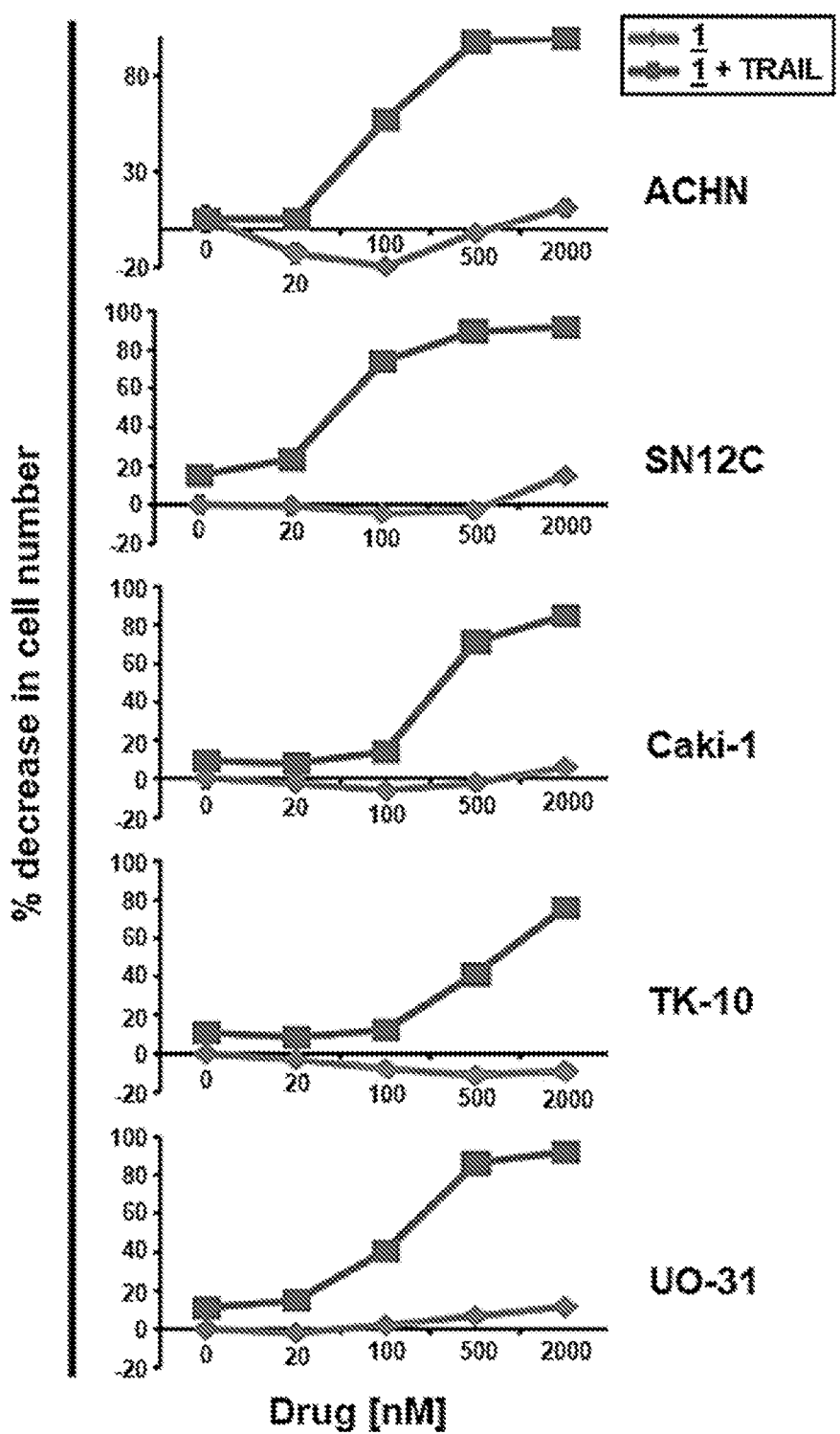

FIG. 8A shows the percentage decrease in cell numbers for ACHN, SN12C, Caki-1, TK-10, and UO-31 cells as a function of concentration of compound 1 in the presence and absence of TRAIL.

Figure 8B:
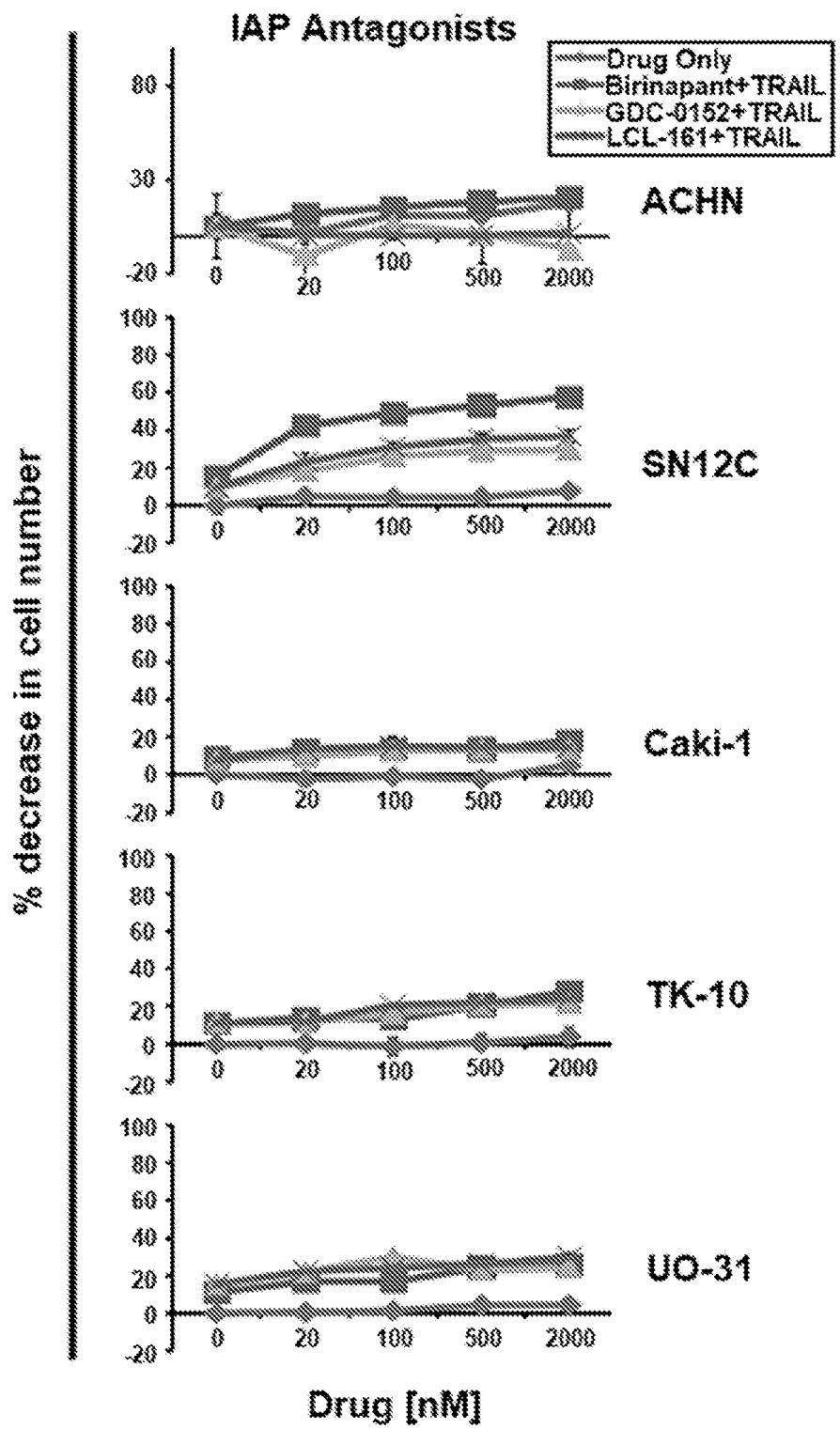

FIG. 8B shows the percentage decrease in cell numbers for ACHN, SN12C, Caki-1, TK-10, and UO-31 cells as a function of concentration of the IAP family antagonists Birinapant, GDC-0152, and LCL-161 in the presence and absence of TRAIL.

Figure 8C:
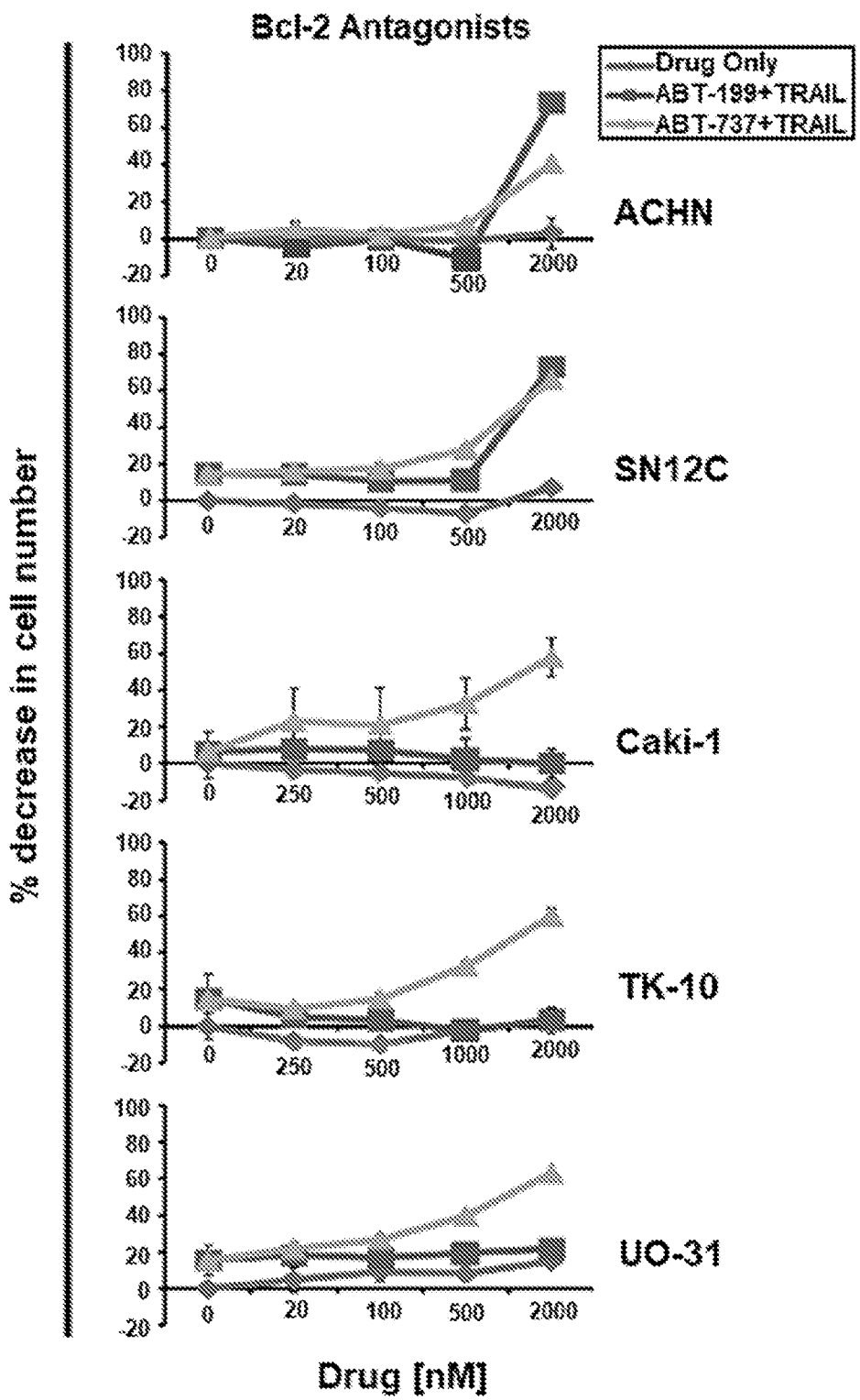

FIG. 8C shows the percentage decrease in cell numbers for ACHN, SN12C, Caki-1, TK-10, and UO-31 cells as a function of concentration of the Bcl-2 family antagonists ABT-199 and ABT-727 in the presence and absence of TRAIL.

Figure 9A:
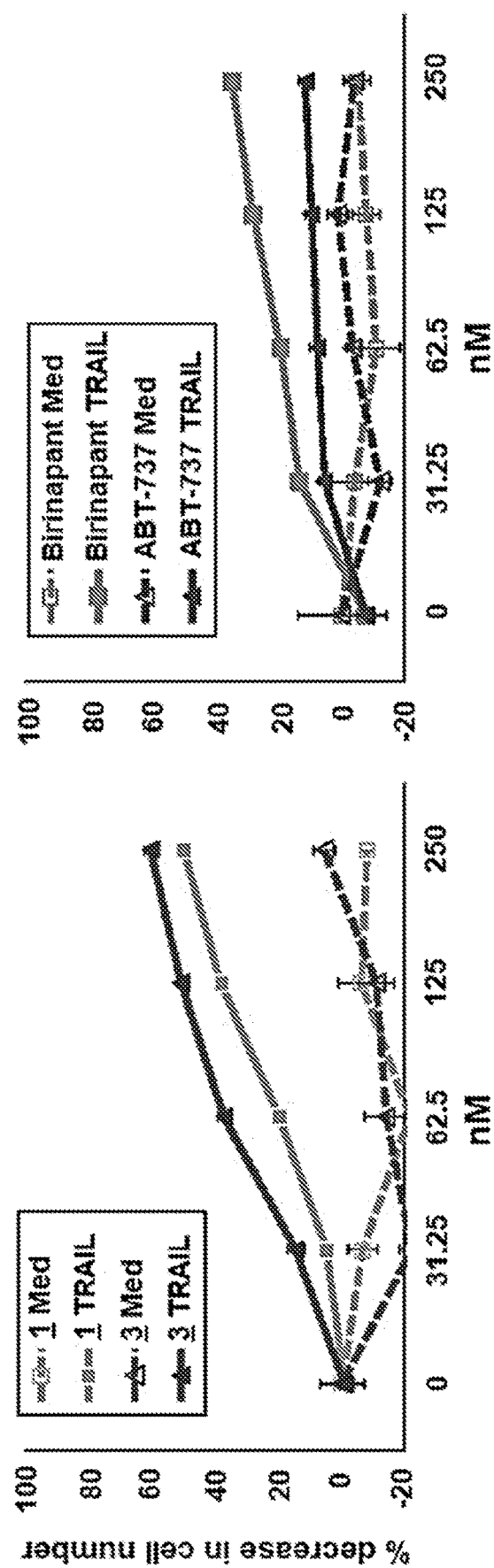

FIG. 9A (left panel) shows the percentage decrease in cell numbers for 888 melanoma cells as a function of concentration of compounds 1 and 3 in the presence and absence of TRAIL. FIG. 9A (right panel) shows the percentage decrease in cell numbers for 888 melanoma cells as a function of concentration of Birinapant and ABT-737 in the presence and absence of TRAIL.

Figure 9B:
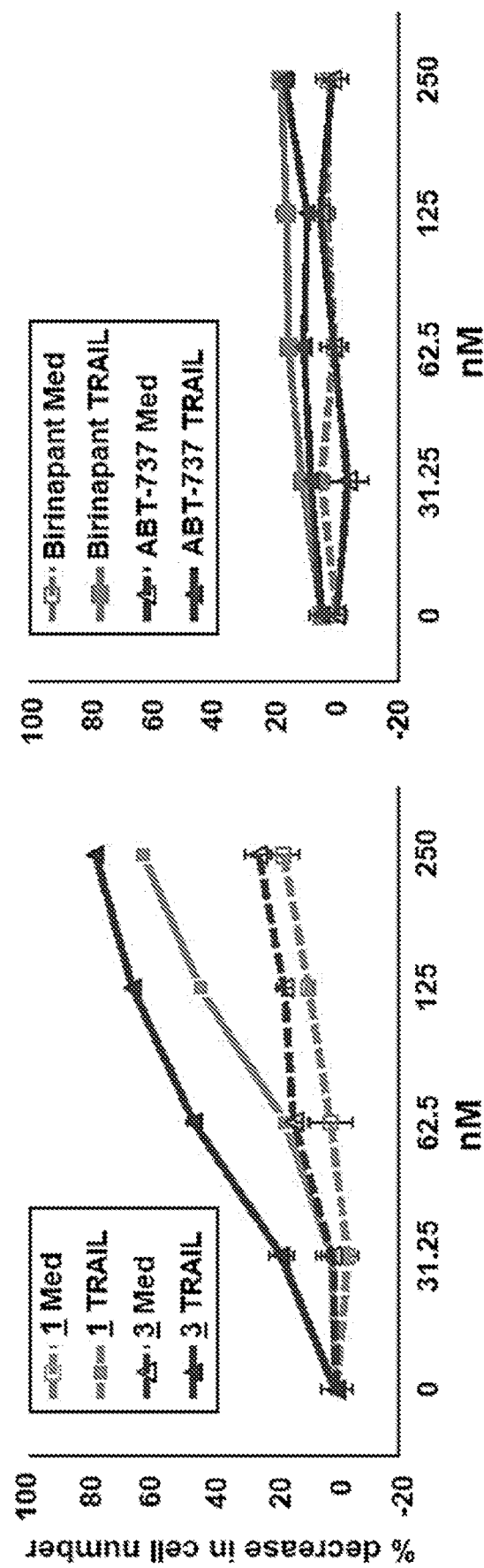

FIG. 9B (left panel) shows the percentage decrease in cell numbers for 1383 melanoma cells as a function of concentration of compounds 1 and 3 in the presence and absence of TRAIL. FIG. 9B (right panel) shows the percentage decrease in cell numbers for 1383 melanoma cells as a function of concentration of Birinapant and ABT-737 in the presence and absence of TRAIL.

Figure 9C:
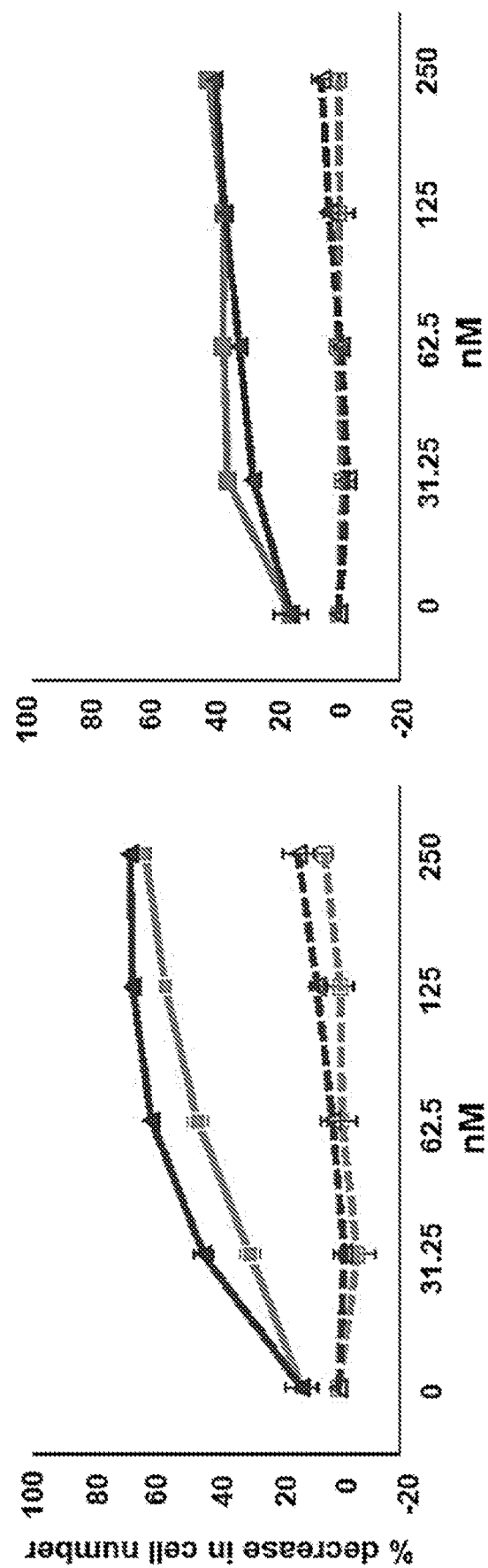

FIG. 9C (left panel) shows the percentage decrease in cell numbers for Baldwin melanoma cells as a function of concentration of compounds 1 and 3 in the presence and absence of TRAIL. FIG. 9C (right panel) shows the percentage decrease in cell numbers for Baldwin melanoma cells as a function of concentration of Birinapant and ABT-737 in the presence and absence of TRAIL.

Figure 10A:
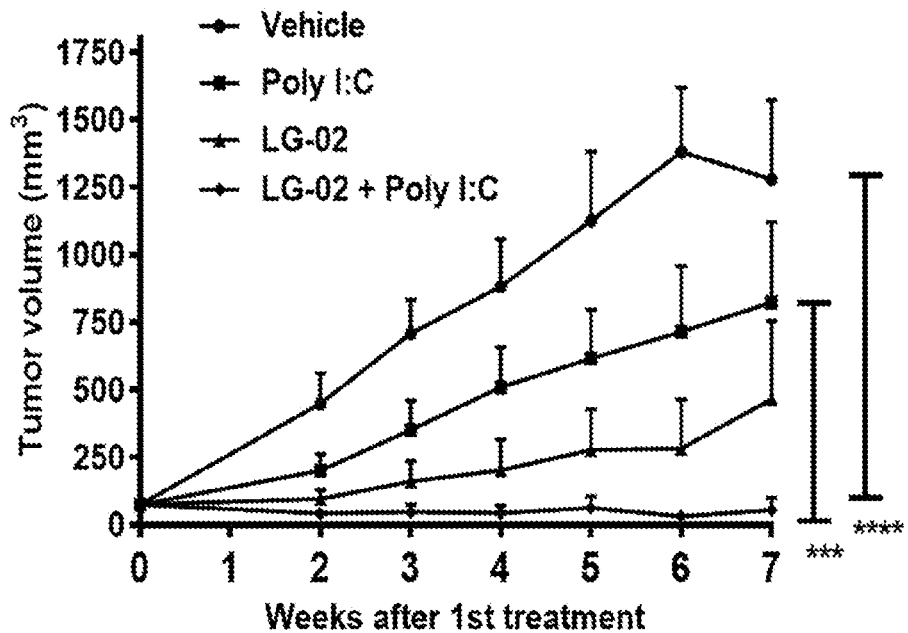

FIG. 10A shows the tumor volume in a xenograft human M14 melanoma model in the period after the first treatment with vehicle, poly (I:C), compound 1, and compound 1+Poly (I:C).

Figure 10B:
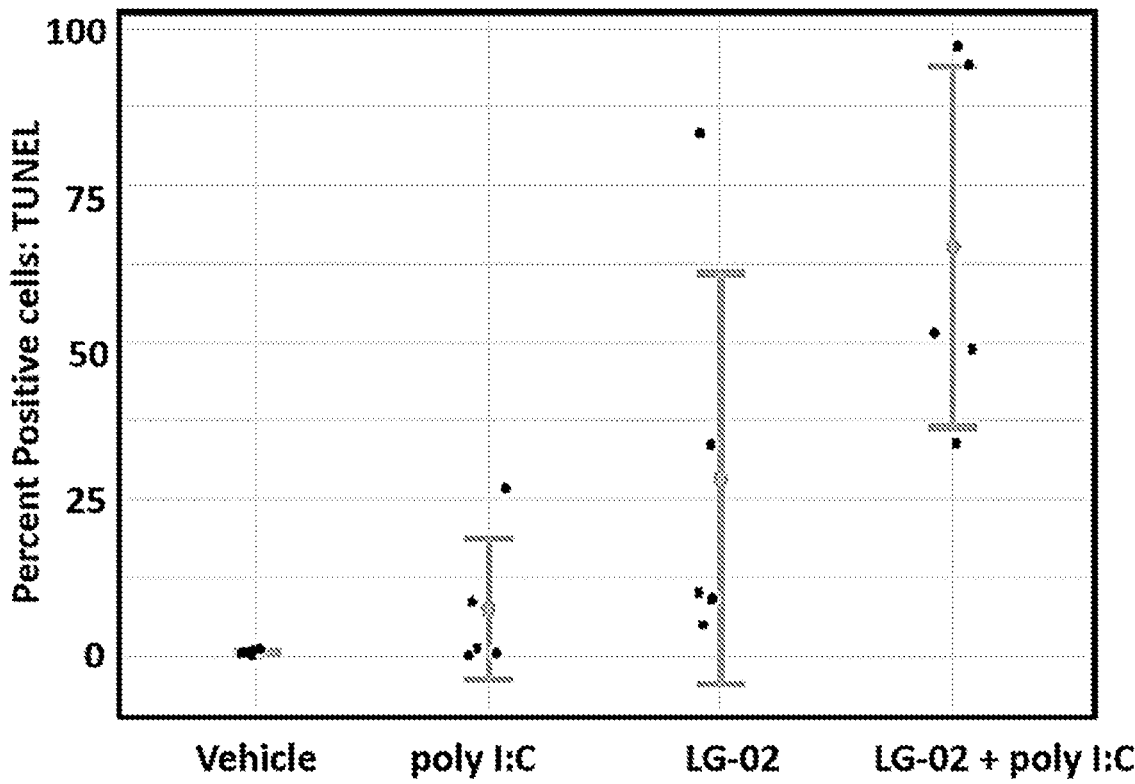

FIG. 10B shows percent positive M14 melanoma cells in TUNEL staining at 24 h after a second injection treated with vehicle, poly (I:C), compound 1, and compound 1+poly (I:C).

Figure 11:
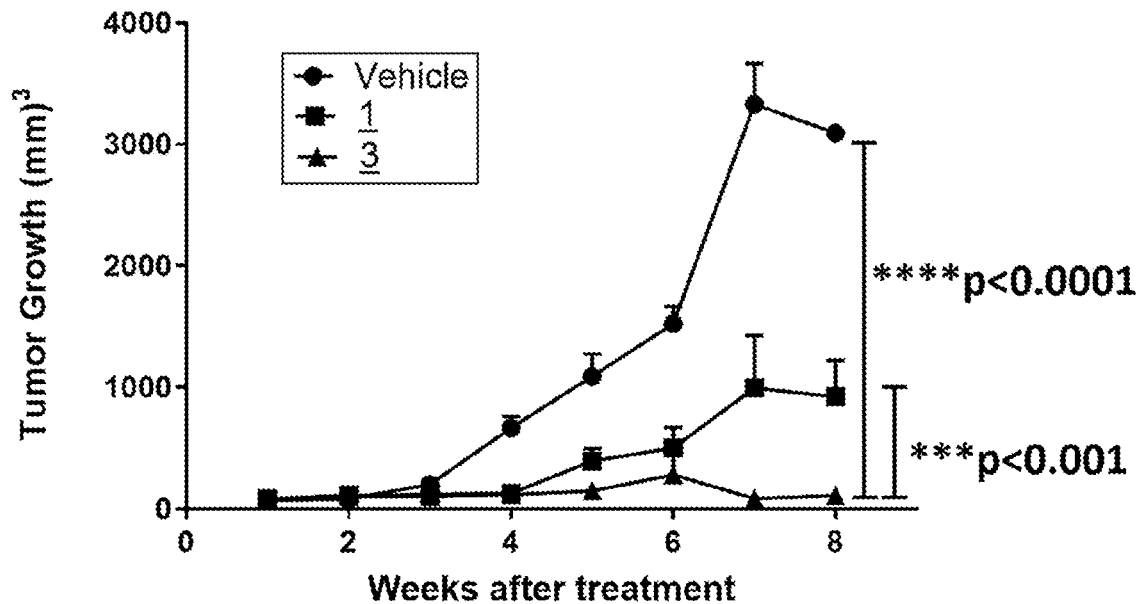

FIG. 11 shows the tumor volume in a xenograft B16F10 melanoma model in the period after the first treatment with vehicle, compound 1, and compound 3.

Figure 12:
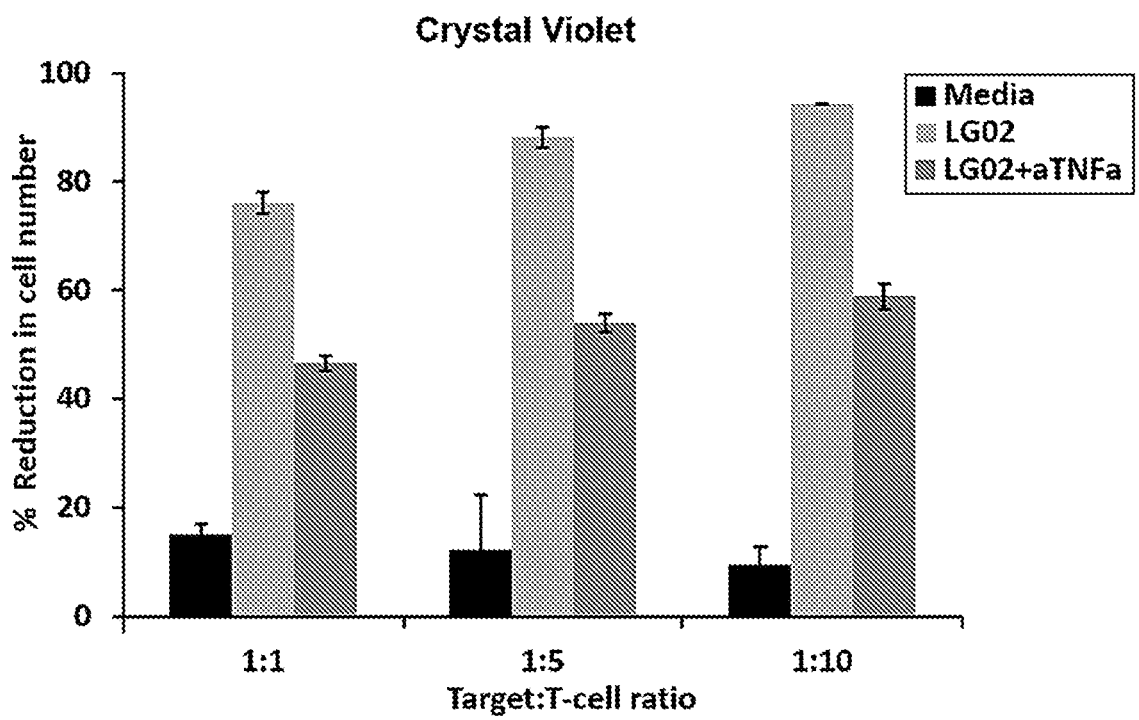

FIG. 12 shows the percentage reduction in cell number of SK-Mel-28 melanoma cells treated with media, compound 1, or a combination of compound 1 and α-TNFα incubated with activated human T cells.

Figure 13:
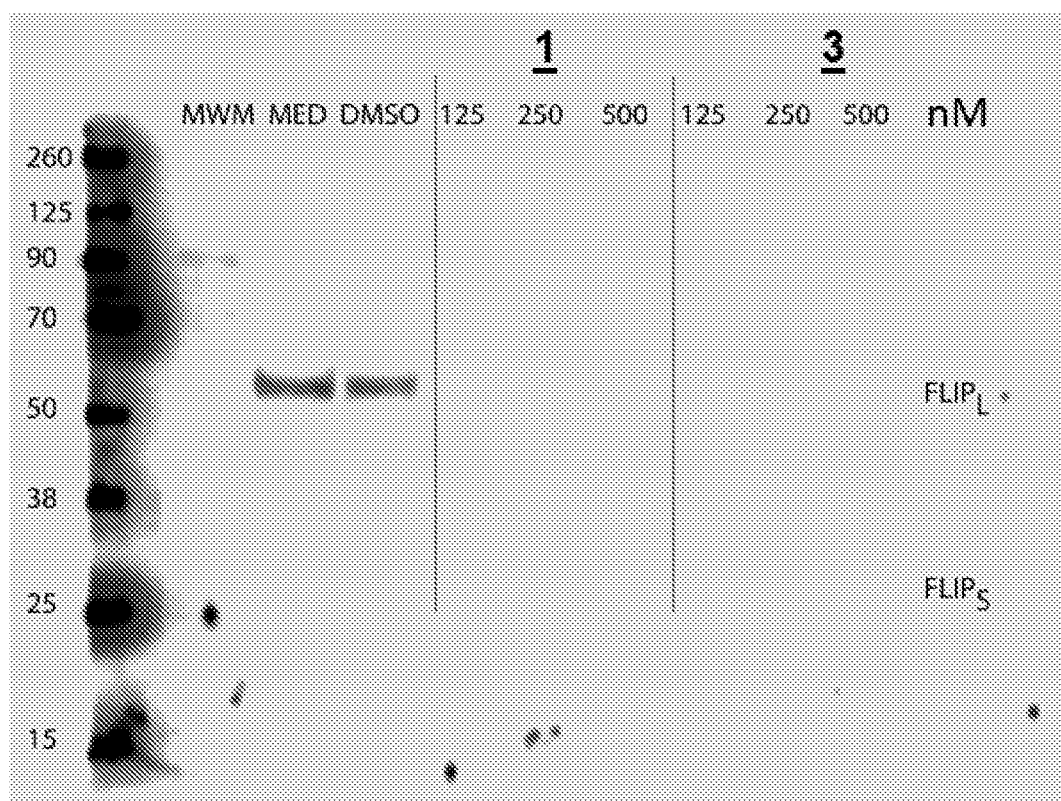

FIG. 13 shows the reduction in cFLIP levels for $FLIP_L$ and $FLIP_S$ in LNCaP prostate cancer cells treated with compound 1 and compound 3.

Figure 14:
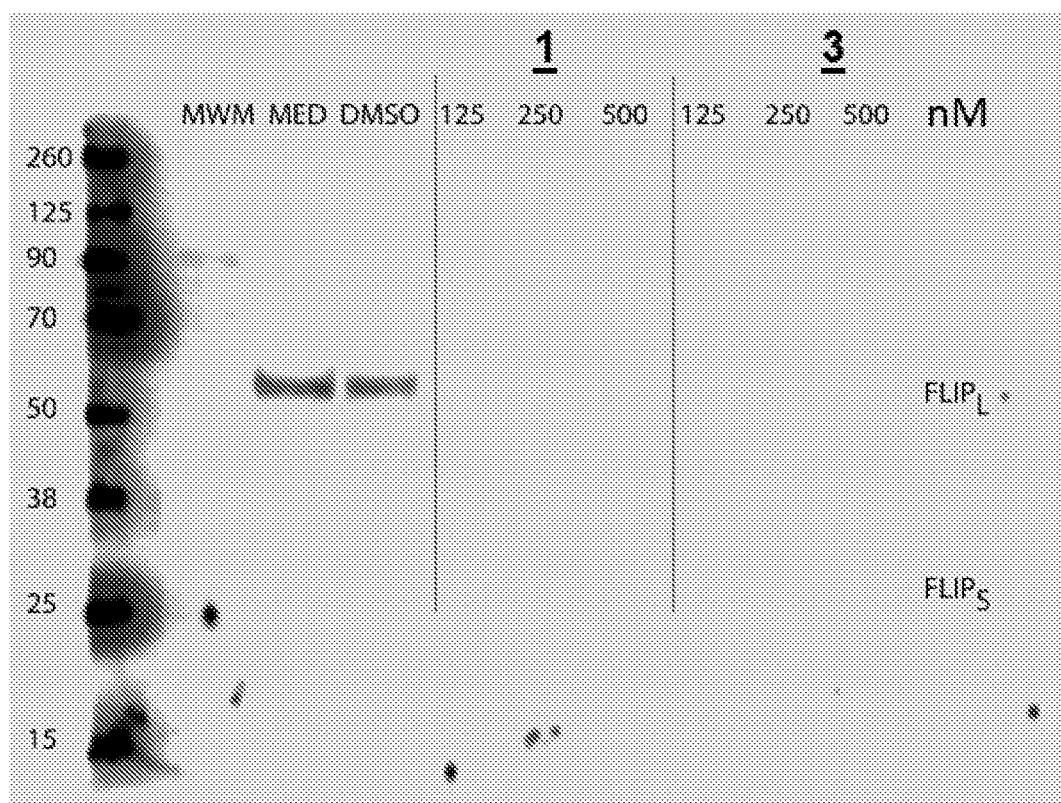

FIG. 14 shows the reduction in cFLIP levels for $FLIP_L$ and $FLIP_S$ in 22Rv1 prostate cancer cells treated with compound 1 and compound 3.

Figure 15:
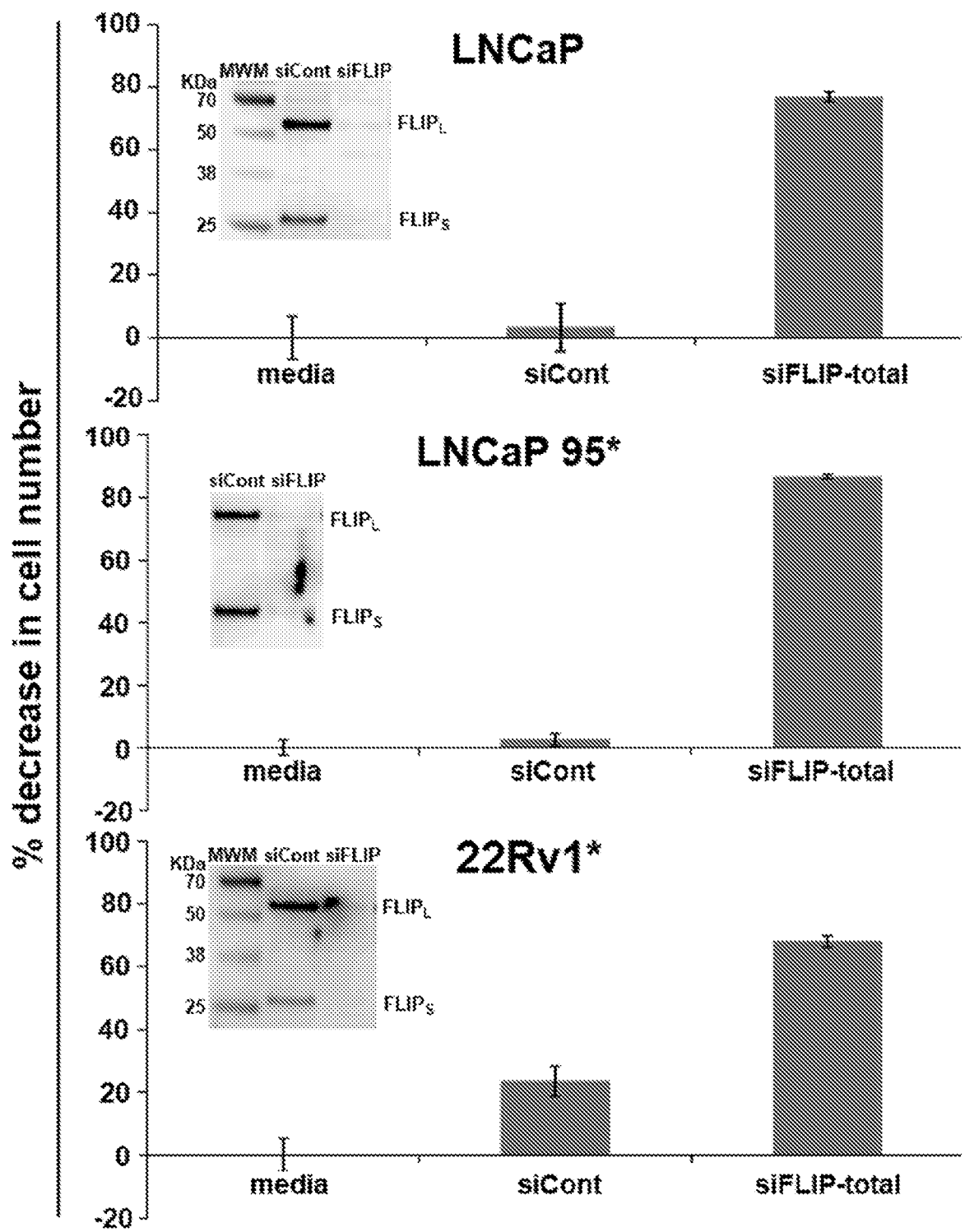

FIG. 15 shows the reduction in cell numbers for LNCaP, LNCaP 95, and 22Rv1 cells upon treatment with si RNA Cont and siRNA FLIP.

Figure 16:
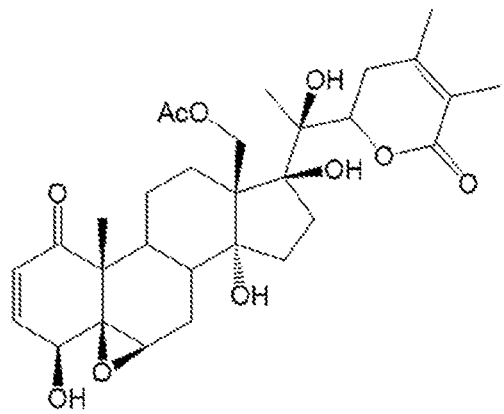

FIG. 16 shows the structure of physachenolide C (PCC).

Figure 17:
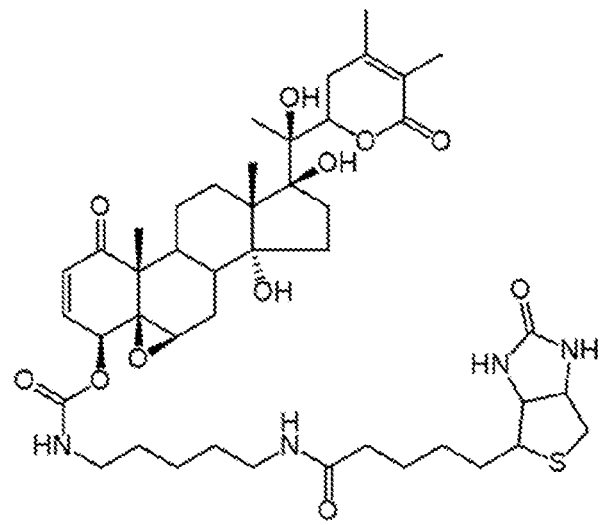

FIG. 17 shows the structure of a biotinylated analog of physachenolide C (Bt PCC).

Figure 18:
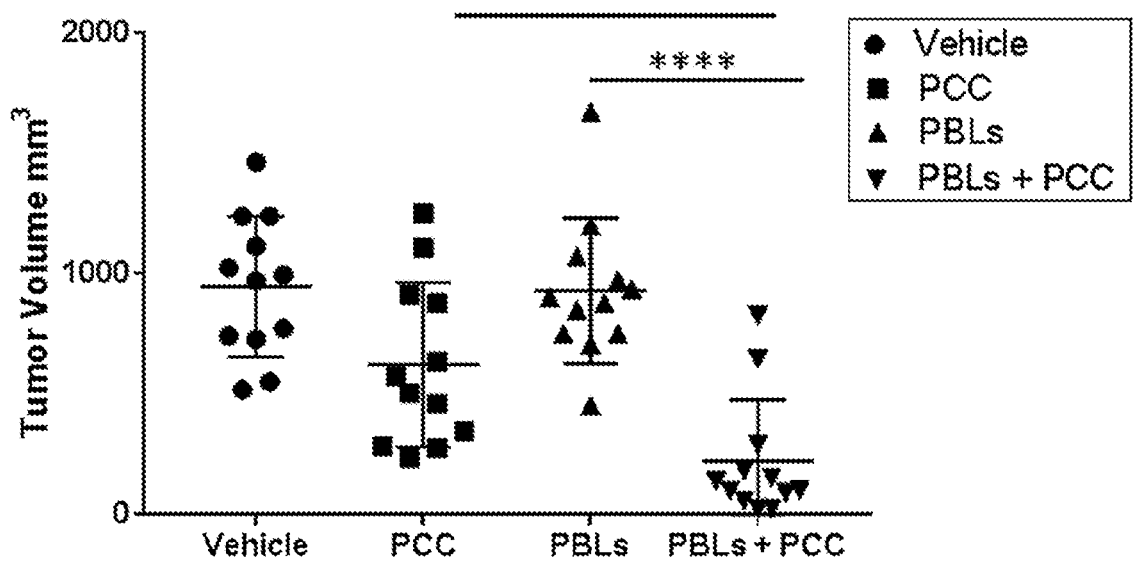

FIG. 18 shows tumor volumes of tumors originating from M14 human melanoma cells in immunodeficient NSG mice after treatment with vehicle, PCC, peripheral blood mononuclear cells (PBLs), or PBLs+PCC.

FIG. 19A shows SDS PAGE gel electrophoresis of elutants from incubation of M14 cell extracts with biotinylated PCC bound to Streptavidin beads.

FIG. 19B shows mass spectrometric analysis of excised gel bands shown in FIG. 18A.

FIG. 19C shows western blotting of excised gel bands shown in FIG. 18A.

Figure 20A:
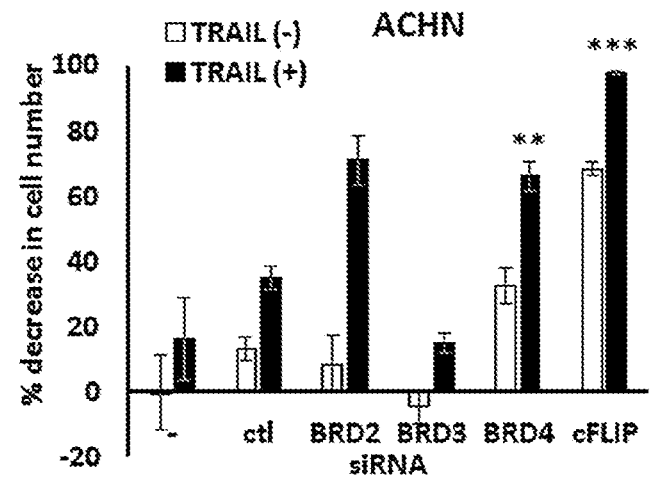

FIG. 20A shows cell numbers for ACHN cells plated in medium and treated with 50 nM siRNA (BRD2, BRD3, and BRD4), then treated with media or 50 ng/mL of TRAIL.

Figure 20B:
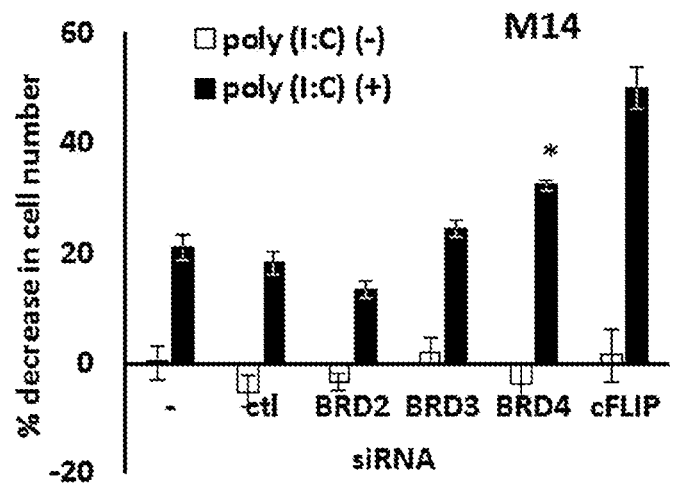

FIG. 20B shows cell numbers for M14 cells plated in medium and treated with 50 nM siRNA (BRD2, BRD3, and BRD4), then treated with media or 10 ug/mL of poly(I:C).

Figure 20C:
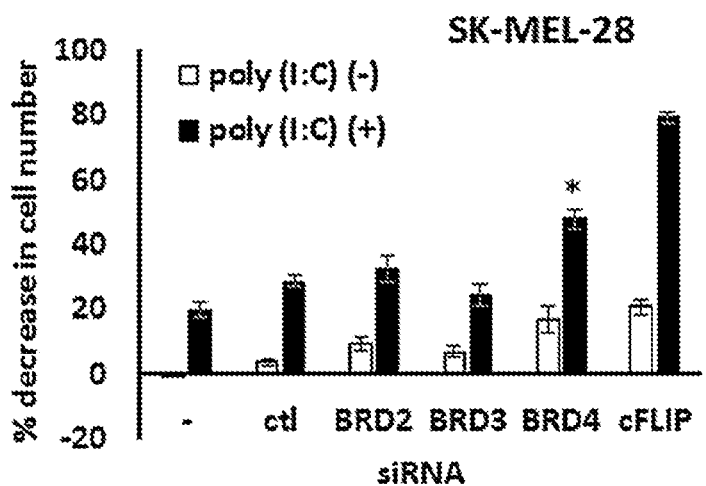

FIG. 20C shows cell numbers for SK-MEL-28 cells plated in medium and treated with 50 nM siRNA (BRD2, BRD3, and BRD4), then treated with media or 10 ug/mL of poly(I:C).

Figure 21:
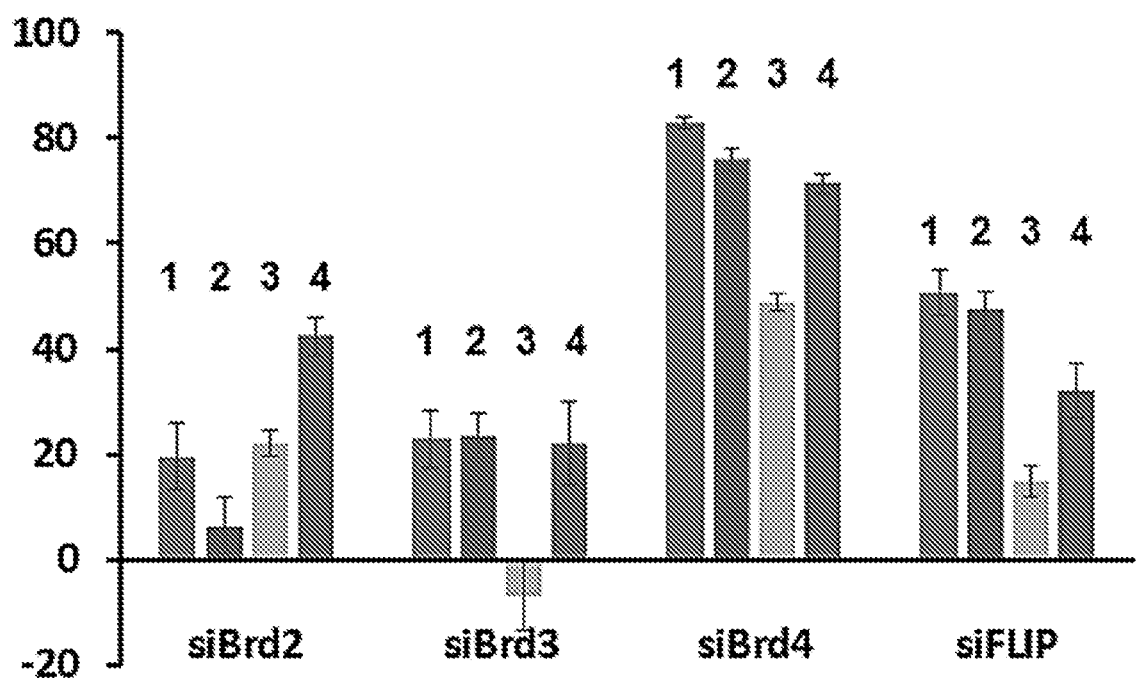

FIG. 21 shows the percent decrease in cell number for prostate cancer cell lines (LNCaP, LNCaP 95, VCaP, and 22Rv1) incubated overnight, transfected with 50 nM siRNA (siBrd2, siBrd3, siBrd4, and siFLIP), and followed by 6 days of incubation. Cell number was determined using an MTS assay.

DETAILED DESCRIPTION OF THE INVENTION

The invention provides a compound of formula (I):

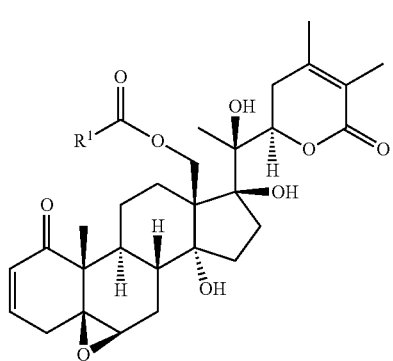

(I)

wherein $R^1$ is $C_2$-$C_{10}$ alkyl, $C_3$-$C_8$ cycloalkyl, $C_6$-$C_{10}$ aryl, $C_6$-$C_{10}$ aryl-$C_1$-$C_{10}$ alkyl, $C_6$-$C_{10}$ aryl-$C_2$-$C_{10}$ alkenyl, monocyclic heteroaryl, bicyclic heteroaryl, monocyclic heteroaryl-$C_1$-$C_{10}$ alkyl, bicyclic heteroaryl-$C_1$-$C_{10}$ alkyl, or 4-alkylenyl-tetrahydro-1H-thieno[3,4-d]imidazol-2(3H)-one, wherein the aryl or heteroaryl portion of $R^1$ is optionally substituted with one or more substituents selected from the group consisting of alkyl, alkoxy, aryl, thioalkoxy, heterocyclyl, and nitro.

In certain embodiments, $R^1$ is $C_2$-$C_{10}$ alkyl.
In certain embodiments, $R^1$ is $C_3$-$C_8$ cycloalkyl.
In certain particular embodiments, $R^1$ is cyclopropyl or cyclohexyl.
In certain embodiments, $R^1$ is optionally substituted $C_6$-$C_{10}$ aryl.
In certain particular embodiments, $R^1$ is

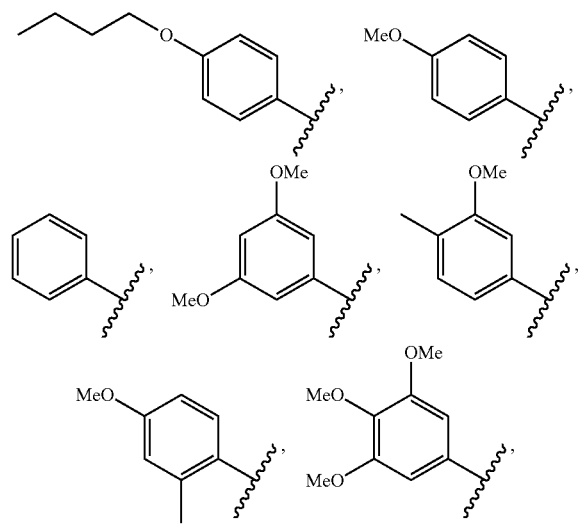

-continued

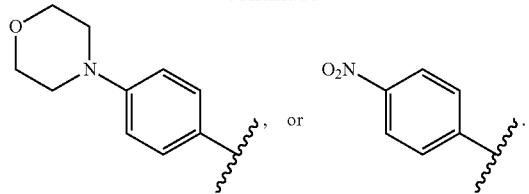

In certain embodiments, $R^1$ is $C_6$-$C_{10}$ aryl-$C_1$-$C_{10}$ alkyl.
In a particular embodiment, $R^1$ is

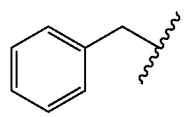

In certain embodiments, $R^1$ is $C_6$-$C_{10}$ aryl-$C_2$-$C_{10}$ alkenyl, wherein the aryl portion is optionally substituted.

In particular embodiments, $R^1$ is

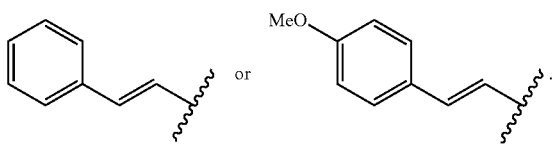 [SMILES: */C=C/c1ccccc1 ; */C=C/c1ccc(OC)cc1]

In certain embodiments, $R^1$ is optionally substituted monocyclic heteroaryl.

In particular embodiments, $R^1$ is

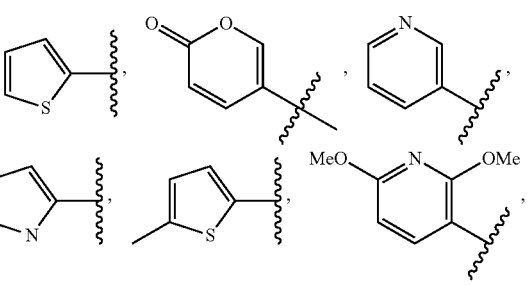

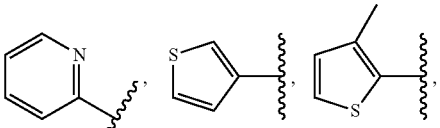

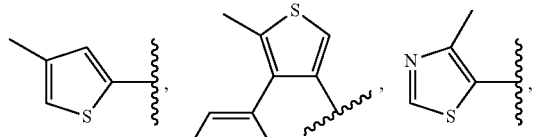

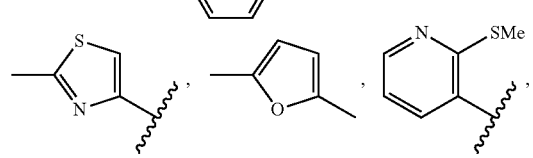

-continued

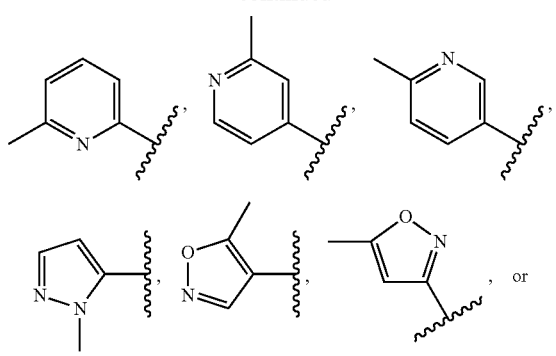

In certain embodiments, $R^1$ is optionally substituted bicyclic heteroaryl.

In particular embodiments, $R^1$ is

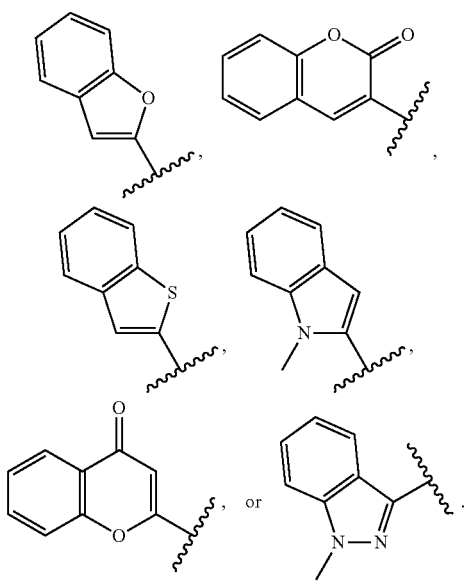

In certain embodiments, $R^1$ is monocyclic heteroaryl-$C_1$-$C_{10}$ alkyl, wherein the heteroaryl portion is optionally substituted.

In a particular embodiment, $R^1$ is

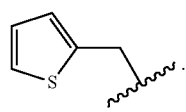 [SMILES: *Cc1cccs1]

In certain embodiments, $R^1$ is 4-alkylenyl-tetrahydro-1H-thieno[3,4-d]imidazol-2(3H)-one.

In a particular embodiment, $R^1$ is

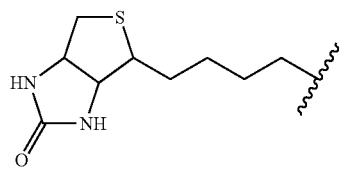

In some embodiments, the invention provides a compound selected from the group consisting of:

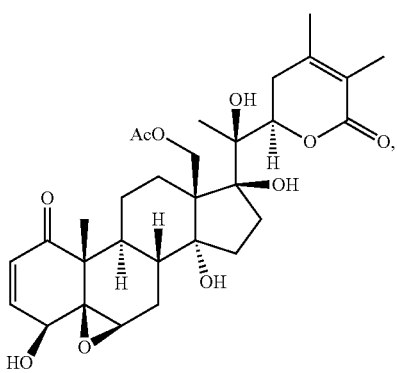

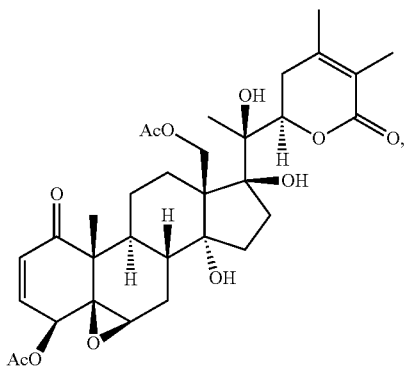

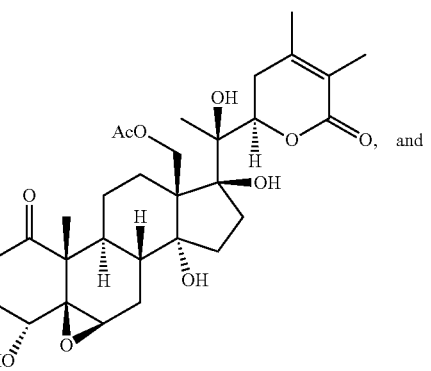

-continued
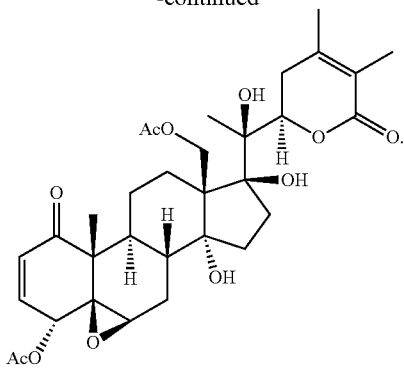
In some embodiments, the invention provides a compound of formula (II):
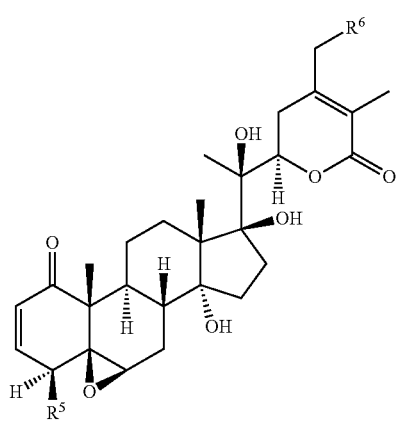
(II)
wherein R⁶ is H and R⁵ is
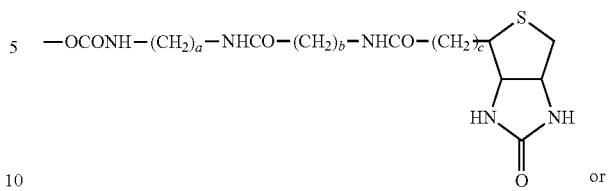
or
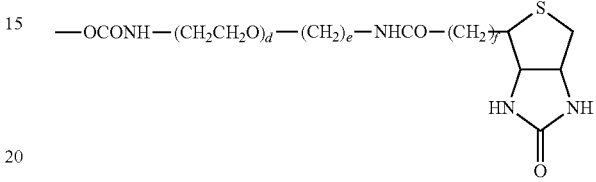
or
wherein R⁵ is H and R⁶ is
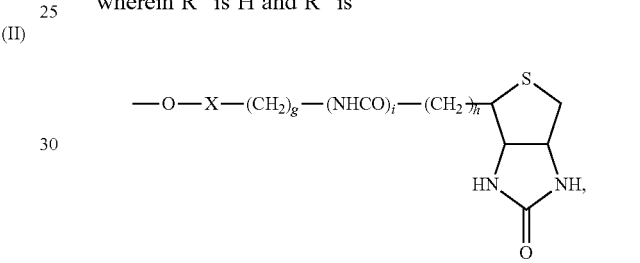
wherein a, b, c, d, e, and f are independently integers of from 1 to 10,
X is NH or absent, and
wherein g and h are integers of from 1 to 5 and i is 0 or 1.
In certain particular embodiments, the compound is:
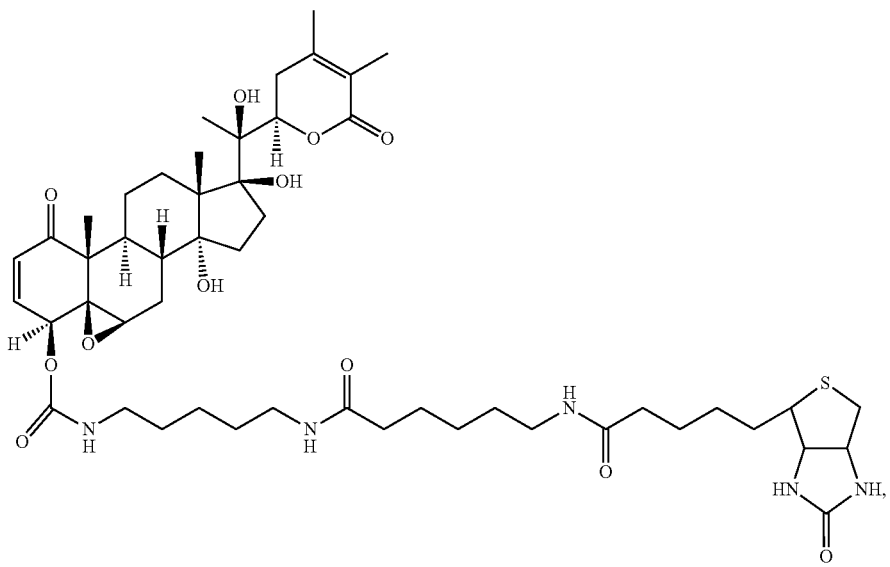

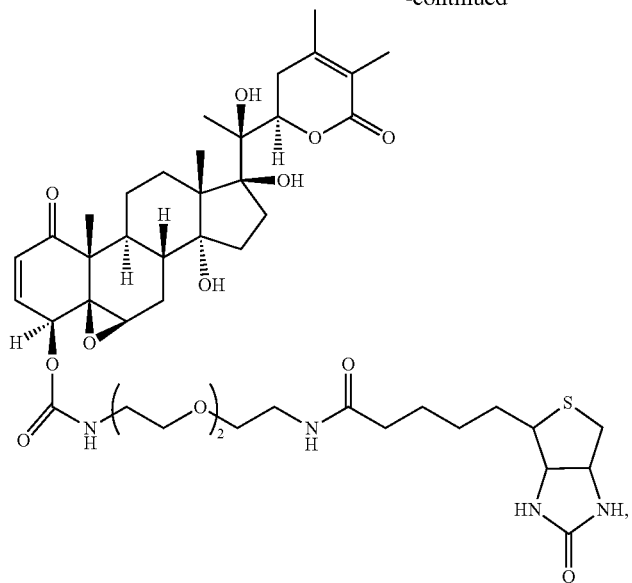
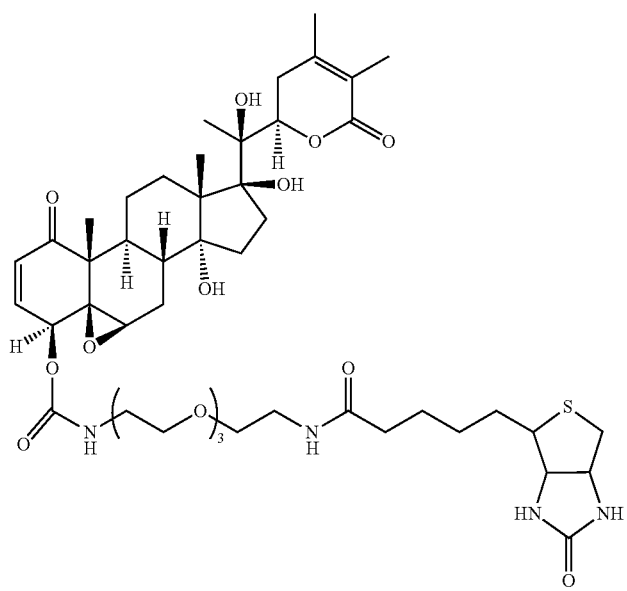
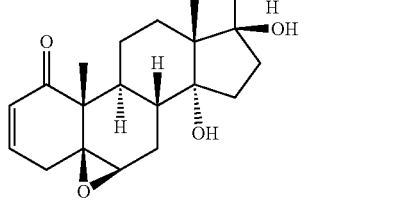 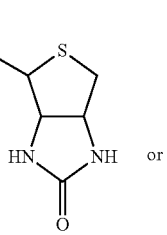 or

-continued

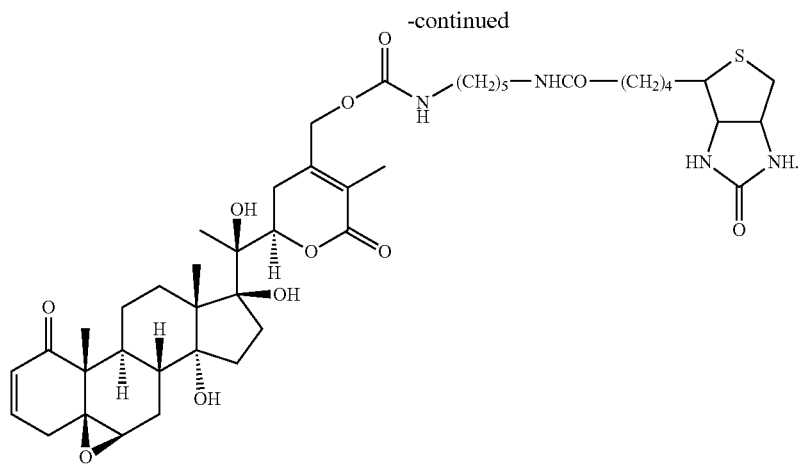

Referring now to terminology used generically herein, the term "alkyl" means a straight-chain or branched alkyl substituent containing from, for example, from 1 to about 10 carbon atoms, e.g., from 1 to about 8 carbon atoms, from 1 to about 6 carbon atoms, from 1 to about 4 carbon atoms, from 2 to about 10 carbon atoms, e.g., from 2 to about 8 carbon atoms, from 2 to about 6 carbon atoms, from 2 to about 4 carbon atoms, or from 1 to 2 carbon atoms. Examples of such substituents include methyl, ethyl, propyl, isopropyl, n-butyl, sec-butyl, isobutyl, tert-butyl, pentyl, isoamyl, hexyl, heptyl, octyl, nonyl, decyl, branched and unbranched versions thereof, and the like.

The term "cycloalkyl," as used herein, means a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The cyclic alkyl groups may be unsubstituted or further substituted with alkyl groups such as methyl groups, ethyl groups, and the like. The term "cycloalkylalkyl," as used herein, refers to an alkyl group linked to a cycloalkyl group and further linked to a molecule via the alkyl group.

The term "halo" or "halogen," as used herein, means a substituent selected from Group VIIA, such as, for example, fluorine, bromine, chlorine, and iodine.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise $4n+2\pi$ electrons, according to Hückel's Rule.

The term "heteroaryl" refers to 3-7 membered rings which are heteroaromatic, comprising carbon and one or more heteroatoms such as O, N, and S, and optionally hydrogen; optionally in combination with one or more aromatic rings. The heteroaryl group can be monocyclic or bicyclic. Examples of monocyclic heteroaryl groups include pyridyl, pyranyl, furanyl, thienyl, furyl, thiopheneyl, purinyl, pyrimidinyl, thiazolyl, thiazolidinyl, thiazolinyl, oxazolyl, isoxazolyl, pyrazolyl, imidazolyl, tetrazolyl, pyrrolyl, and tetrazinyl. Examples of bicyclic heteroaryl groups include benzoxazolyl, benzothiopheneyl, indolyl, indazolyl, quinolinyl, and isoquinolinyl.

The term "arylalkyl," as used herein, refers to an alkyl group linked to a $C_6$-$C_{10}$ aryl ring and further linked to a molecule via the alkyl group. The terms monocyclic heteroaryl-$C_1$-$C_{10}$ alkyl and bicyclic heteroaryl-$C_1$-$C_{10}$ alkyl, as used herein, refers to an alkyl group linked to a monocyclic heteroaryl or bicyclic heteroaryl ring and further linked to a molecule via the alkyl group Whenever a range of the number of atoms in a structure is indicated (such as a $C_1$-$C_{12}$, $C_1$-$C_8$, $C_1$-$C_6$, $C_1$-$C_4$, or $C_2$-$C_{12}$, $C_2$-$C_8$, $C_2$-$C_6$, $C_2$-$C_4$ alkyl, alkenyl, alkynyl, etc.), it is specifically contemplated that any sub-range or individual number of carbon atoms falling within the indicated range also can be used. Thus, for instance, the recitation of a range of 1-8 carbon atoms (such as $C_1$-$C_8$), 1-6 carbon atoms (such as $C_1$-$C_6$), 1-4 carbon atoms (such as $C_1$-$C_4$), 1-3 carbon atoms (such as $C_1$-$C_3$), or 2-8 carbon atoms (such as $C_2$-$C_8$) as used with respect to any chemical group (such as alkyl, alkylamino, etc.) referenced herein encompasses and specifically describes 1, 2, 3, 4, 5, 6, 7, 8, 9, 10, 11, or 12 carbon atoms, and combinations thereof, as appropriate, as well as any sub-range thereof (such as 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate). Similarly, the recitation of a range of 6-10 carbon atoms (such as, $C_6$-$C_{10}$) as used with respect to any chemical group (such as, aryl) referenced herein encompasses and specifically describes 6, 7, 8, 9, and/or 10 carbon atoms, as appropriate, as well as any sub-range thereof (such as, 6-10 carbon atoms, 6-9 carbon atoms, 6-8 carbon atoms, 6-7 carbon atoms, 7-10 carbon atoms, 7-9 carbon atoms, 7-8 carbon atoms, 8-10 carbon atoms, and/or 8-9 carbon atoms, etc., as appropriate).

By "enhancing the response" is meant that the apoptosis inducing ligand has a greater effect (e.g., at least a 5% increase, at least a 10% increase, at least a 20% increase, at least a 30% increase, at least a 40% increase, at least a 50% increase, at least a 60% increase, at least a 70% increase, at least an 80% increase, or higher) in the presence of the sensitizer than in the absence of the sensitizer. Since the apoptosis inducing ligand causes apoptosis in cancer cells, if a sensitizer sensitizes the cancer cells to the apoptosis inducing ligand, the cancerous cell is more susceptible to apoptosis triggered by the apoptosis inducing ligand, thereby making it more likely to experience programmed cell death as a result of use of the inventive method.

In certain embodiments, the invention provides a method of synergistically enhancing the response of cancer cells to treatment with an apoptosis inducing ligand, which method comprises contacting the cancer cells with an effective amount of an apoptosis inducing ligand in conjunction with an effective amount of a sensitizer, whereby a synergistic enhancement of the response is obtained. The sensitizer is a compound of (I):

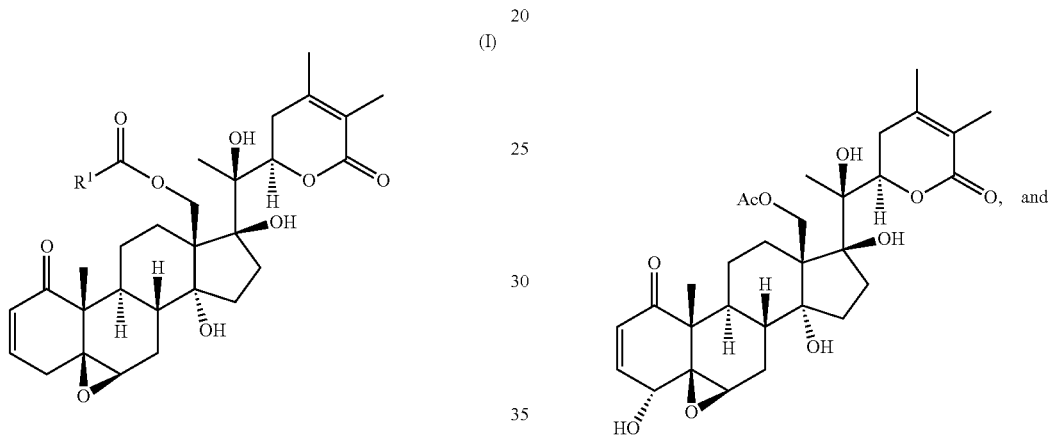

wherein $R^1$ is $C_2$-$C_{10}$ alkyl, $C_3$-$C_8$ cycloalkyl, $C_6$-$C_{10}$ aryl, $C_6$-$C_{10}$ aryl-$C_1$-$C_{10}$ alkyl, $C_6$-$C_{10}$ aryl-$C_2$-$C_{10}$ alkenyl, monocyclic heteroaryl, bicyclic heteroaryl, monocyclic heteroaryl-$C_1$-$C_{10}$ alkyl, bicyclic heteroaryl-$C_1$-$C_{10}$ alkyl, or 4-alkylenyl-tetrahydro-1H-thieno[3,4-d]imidazol-2(3H)-one, wherein the aryl or heteroaryl portion of $R^1$ is optionally substituted with one or more substituents selected from the group consisting of alkyl, alkoxy, aryl, thioalkoxy, heterocyclyl, and nitro, wherein $R^1$ is as described herein, or a compound selected from the group consisting of:

In certain embodiments, the invention provides a method of inducing apoptosis in cancer cells in a mammal that are resistant to treatment with an apoptosis-inducing ligand, comprising (a) sensitizing the cancer cells by contacting the cancer cells with a sensitizer, and (b) contacting the cancer cells with an effective amount of an apoptosis-inducing ligand, wherein apoptosis is induced in the cancer cells. The sensitizer is a compound of formula (I):

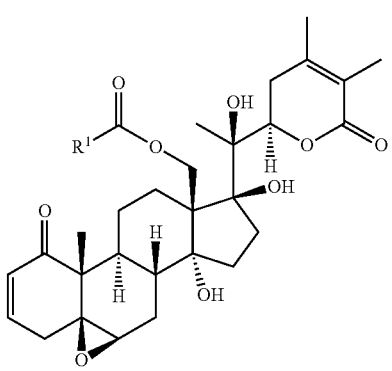

(I)

wherein $R^1$ is $C_2$-$C_{10}$ alkyl, $C_3$-$C_8$ cycloalkyl, $C_6$-$C_{10}$ aryl, $C_6$-$C_{10}$ aryl-$C_1$-$C_{10}$ alkyl, $C_6$-$C_{10}$ aryl-$C_2$-$C_{10}$ alkenyl, monocyclic heteroaryl, bicyclic heteroaryl, monocyclic heteroaryl-$C_1$-$C_{10}$ alkyl, bicyclic heteroaryl-$C_1$-$C_{10}$ alkyl, or 4-alkylenyl-tetrahydro-1H-thieno[3,4-d]imidazol-2(3H)-one, wherein the aryl or heteroaryl portion of $R^1$ is optionally substituted with one or more substituents selected from the group consisting of alkyl, alkoxy, aryl, thioalkoxy, heterocyclyl, and nitro, wherein $R^1$ is as described herein, or a compound selected from the group consisting of:

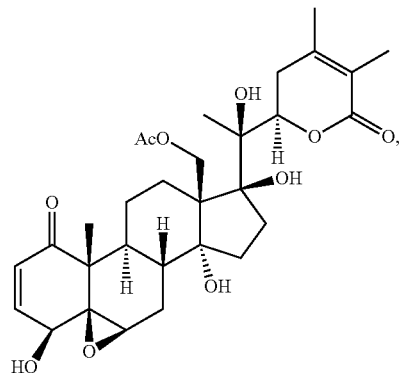

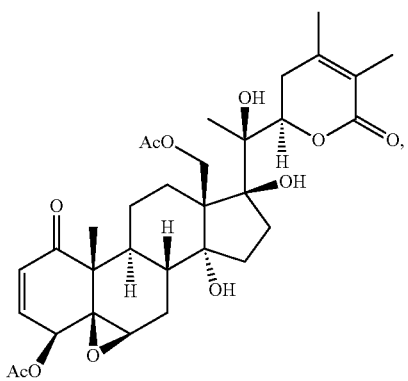

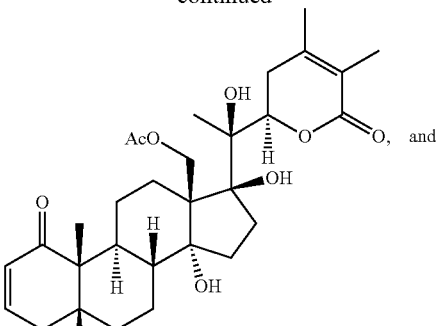

and

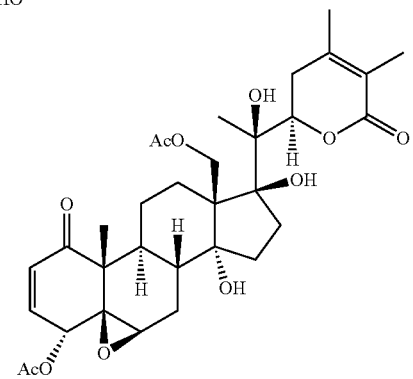

As used herein, the term "synergistic" refers to a combination of compounds of the invention and/or a combination of a compound or compounds of the invention and another therapy (e.g., a prophylactic or therapeutic agent), including one which has been or is currently being used to prevent, manage or treat a disorder (e.g., a proliferative disorder or cancer), which combination is more effective than the additive effects of the individual compounds or therapies. A synergistic effect of a combination of therapies (e.g., a combination of prophylactic or therapeutic agents) can permit the use of lower dosages of one or more of the therapies and/or less frequent administration of the therapies to a subject with a disorder (e.g., a proliferative disorder or cancer). The ability to utilize lower dosages of a therapy (e.g., a prophylactic or therapeutic agent) and/or to administer the therapy less frequently can reduce the toxicity associated with the administration of the therapy to a subject without reducing the efficacy of the therapy in the prevention, management or treatment of a disorder (e.g., a proliferative disorder or cancer). In addition, a synergistic effect can result in improved efficacy of agents in the prevention, management or treatment of a disorder (e.g., a proliferative disorder or cancer). Moreover, a synergistic effect of a combination of therapies (e.g., a combination of prophylactic or therapeutic agents) can avoid or reduce adverse or unwanted side effects associated with the use of either therapy alone.

The term "synergistic" is contrasted with the term "additive" in that a combination of an agent having an additive effect and an apoptosis inducing ligand exhibits an effect that is simply the sum of the effect produced by the agent and the apoptosis inducing ligand when administered individually.

As used herein, the term "apoptosis inducing ligand" refers more specifically to a "apoptosis inducing receptor agonist" and is intended to mean an agent capable of stimulating by direct or indirect contact the proapoptotic response mediated by the apoptosis inducing receptors. In certain embodiments, the apoptosis inducing receptor is a cytokine receptor, for example, a TNF receptor. In an embodiment, the apoptosis inducing ligand is TRAIL. TRAIL itself binds to DR4 and DR5. An agonist TRAIL receptor antibody would bind to TRAIL receptor and trigger an apoptotic response. In embodiments, the apoptosis inducing ligand is selected from the group consisting of TRAIL, TNF-α, FasL, an anti-DR4 antibody, and an anti-DR5 antibody.

TRAIL (also referred to as ApoL2) is tumor necrosis factor-α-related apoptosis-inducing ligand and is a widely expressed member of the tumor necrosis factor (TNF) superfamily. TRAIL ligand exists in two forms: as a type II membrane protein expressed on the surface of certain lymphoid cells, and as a cleaved, soluble protein that is detectable in serum. For the purposes of the present invention, soluble recombinant TRAIL is suitable for use and is available from several vendors such as Peprotech, Inc. (Rocky Hill, NJ). The percent growth reduction in treated cells is thought to be the result of apoptosis induced by the death receptor ligand.

Agonist antibodies directed against the death receptors TRAIL-R1 and/or TRAIL-R2 also can be used in conjunction with the method of the present invention. Exemplary agonist antibodies that may be used in combination with the method of the present invention include those described in U.S. Pat. No. 7,244,429; in U.S. Patent Application Publication Nos. 2007/0179086, 2002/0004227, 2006/0269554, 2005/0079172, 2007/0292411, 2006/0270837, 2006/0269555, 2004/0214235, and 2007/0298039; and in International Patent Publications WO2006/017961 and WO98/51793. Each of these publications is hereby incorporated by reference in its entirety. In addition, anti-DR4 and anti-DR5 antibodies are commercially available from Sigma Aldrich (St. Louis, MO) and Enzo Life Sciences (Farmingdale, NY). In preferred embodiments, compounds of the invention are used in combination with one or more of these TRAIL receptor agonist antibodies for the treatment of cancer and other neoplasms.

Examples of suitable antibodies include purified soluble monoclonal antibody which specifically binds TRAIL receptor DR5, wherein the antibody has in vitro cell death-inducing activity in the absence of crosslinking by a secondary antibody and at concentrations less than 1 micromol/ml in target cells expressing DR5, and wherein the antibody has in vivo cell death-inducing activity in target cells expressing DR5, and wherein the antibody does not bind TRAIL receptor DR4, DcR1, or DcR2.

In certain embodiments, the apoptosis inducing receptor is a toll-like receptor ("TLR"). TLRs are a class of proteins that play a key role in the innate immune system. The TLRs include TLR1, TLR2, TLR3, TLR4, TLR5, TLR6, TLR7, TLR8, TLR9, TLR10, TLR11, TLR12, and TLR13, although TLR11, TLR12, and TLR13 are not found in humans. In these embodiments, the apoptosis inducing ligand is a TLR ligand. In a preferred embodiment, the TLR ligand is a ligand for TLR3. Non-limiting examples of suitable TLR ligands include double stranded RNA, polyinosine-polycytidylic acid ("poly I:C"), mRNA, and tRNA. In a preferred embodiment, the TLR ligand is poly (I:C). Poly I:C is a synthetic mismatched double-stranded RNA with one strand being a polymer of inosinic acid and the other a polymer of cytidylic acid being annealed to each other. Poly I:C is available in a range of chain lengths and molecular weights. Poly I:C is commercially available from InvivoGen (San Diego, CA).

In some embodiments, the compounds of the invention can be administered in combination with immunotherapeutic approaches to cancer wherein anti-cancer T cells play a critical role, such as checkpoint inhibition, adoptive T cell transfer, CAR T cell therapy, and the like. In these embodiments, the anti-cancer T cells locally produce various death ligands (i.e., apoptosis inducing ligands) whose tumor destructive capacity can be enhanced by the inventive compounds. Thus, the inventive compounds can sensitize the cancer cells to apoptosis by death ligands that are products of the infiltrating T cells or other local immune cells. The anti-cancer T cells can effectively be the delivery vehicle for multiple death ligands.

In certain embodiments, the invention provides a method of synergistically enhancing the response of cancer cells in a mammal to treatment with anti-cancer T cells, wherein the anti-cancer T cells produce at least one apoptosis inducing ligand, which method comprises administering to the mammal an effective amount of a compound of the invention, and administering an effective amount of anti-cancer T cells, whereby a synergistic enhancement of the response is obtained.

In certain embodiments, the invention provides a method of inducing apoptosis in cancer cells in a mammal that are resistant to treatment with anti-cancer T cells, wherein the anti-cancer T cells produce at least one apoptosis inducing ligand, which method comprises administering to the mammal an effective amount of a compound of a compound of the invention, and administering an effective amount of an anti-cancer T cells, whereby a synergistic enhancement of the response is obtained.

In certain embodiments, the method of synergistically enhancing the response of cancer cells in a mammal to treatment with an apoptosis-inducing ligand or of inducing apoptosis in cancer cells in a mammal that are resistant to treatment with an apoptosis-inducing ligand further comprises administering to the mammal a Smac mimetic, a Bcl-2 antagonist, or a combination thereof. The Smac mimetic or Bcl-2 antagonist can be any suitable Smac mimetic or Bcl-2 antagonist. In certain embodiments, the Smac mimetic is Birinapant, GDC-015, or LCL-161. In certain embodiments, the Bcl-2 antagonist is ABT-199, ABT-737, or Venetoclax.

Desirably, the combination of a compound of the invention and Smac mimetic and/or Bcl-2 antagonist exhibits a synergistic effect in sensitization of cancer cells to treatment with the apoptosis-inducing ligand or to induction of apoptosis when the cancer cells are resistant to treatment with the apoptosis-inducing ligand, as compared to treatment with a compound of the invention Smac mimetic and/or Bcl-2 antagonist.

Any method known in the art can be used to measure the enhancement of the response to cancer cells to treatment with an apoptosis-inducing ligand. In addition, any known method known in the art can be used to determine the induction of apoptosis. The examples section of the present specification describes exemplary methods. For example, the growth inhibition of cancer cells can be determined by measurement of the decrease in cell viability by use of the tetrazolium/formazan assay ("XTT assay") as described in Scudiero et al., *Cancer Res.* 48(17): 4827-4833 (1988), or by use of the sulphorhodamine B protein staining assay ("SRB protein stain") as described in Skehan et al., *J. Natl. Cancer Inst.* 82(13): 1107-1112 (1990) or in Vichai et al., *Nat. Protoc* 1(3): 1112-1116. Another suitable assay for the growth inhibition of cancer cells is the MTS cell proliferation colorimetric assay. The MTS method is based on the reduction of MTS tetrazolium compound by viable cells to generate a colored formazan product that is soluble in cell culture media. This conversion is thought to be carried out by NAD(P)H-dependent dehydrogenase enzymes in metabolically active cells. The formazan dye produced by viable cells can be quantified by measuring the absorbance at 490-500 nm.

The cancer cells in a human can be contacted with an apoptosis-inducing ligand in conjunction with a sensitizer by administering to the human a formulation containing an effective amount of the sensitizer and a formulation containing the apoptosis-inducing ligand. In some embodiments, the sensitizer can be present in the same formulation as the apoptosis-inducing ligand so that the administration can be simultaneous. Any of the sensitizers of the invention can be used in combination with an apoptosis-inducing ligand, e.g., simultaneously, sequentially, e.g., before or after the apoptosis-inducing ligand, or cyclically. In some embodiments, it is suitable to administer two or more separate and distinct formulations, one of which contains the sensitizer and the other contains the apoptosis-inducing ligand. The separate and distinct formulations can be administered simultaneously, or the formulations can be administered separately at different time periods. For example, in preferred embodiments, the formulation containing the sensitizer can be administered about 1 hour (e.g., about 2 hours, or about 3 hours, or about 4 hours, or about 8 hours, or about 24 hours) prior to administration of the formulation containing the apoptosis-inducing ligand. In preferred embodiments, the apoptosis-inducing ligand is administered parenterally in the form of a suitable parenteral formulation, while the sensitizer can be administered in the form of any suitable formulation. Suitable formulations include oral, aerosol, nasal, pulmonary, parenteral, subcutaneous, intravenous, intramuscular, intraperitoneal, intrathecal, intratumoral, topical, rectal, and vaginal formulations.

The pharmaceutical composition can be administered parenterally, e.g., intravenously, subcutaneously, intradermally, or intramuscularly. Thus, the invention provides compositions for parenteral administration that comprise a solution or suspension of the sensitizer and/or the apoptosis-inducing ligand dissolved or suspended in an acceptable carrier suitable for parenteral administration, including aqueous and non-aqueous isotonic sterile injection solutions.

Overall, the requirements for effective pharmaceutical carriers for parenteral compositions are well known to those of ordinary skill in the art. See, e.g., Banker and Chalmers, eds., *Pharmaceutics and Pharmacy Practice*, J. B. Lippincott Company, Philadelphia, pp. 238-250 (1982), and Toissel, *ASHP Handbook on Injectable Drugs*, $4^{th}$ ed., pp. 622-630 (1986). Such solutions can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The sensitizer and/or apoptosis-inducing ligand may be administered in physiologically acceptable ampoules in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-beta-aminopropionates, and 2-alkyl-imidazoline quaternary ammonium salts, and (e) mixtures thereof.

The parenteral formulations can contain preservatives and buffers. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Topical formulations, including those that are useful for transdermal drug release, are well-known to those of skill in the art and are suitable in the context of the invention for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some embodiments, the composition contains at least one sensitizer and a suitable vehicle or carrier. It may also contain other components, such as an anti-irritant. The carrier can be a liquid, solid or semi-solid. In embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

Formulations suitable for oral administration can consist of (a) liquid solutions, such as a therapeutically effective amount of the sensitizer dissolved in diluents, such as water, saline, or orange juice, (b) capsules, sachets, tablets, lozenges, and troches, each containing a predetermined amount of the active ingredient, as solids or granules, (c) powders, (d) suspensions in an appropriate liquid, and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The sensitizer, alone or in combination with other suitable components, can be made into aerosol formulations to be administered via inhalation. The compounds are preferably supplied in finely divided form along with a surfactant and propellant. Typical percentages of a sensitizer are 0.01%-20% by weight, preferably 1%-10%. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25%-5%. The balance of the composition is ordinarily propellant. A carrier can also be included as desired, e.g., lecithin for intranasal delivery. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Additionally, the sensitizer may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the sensitizer, such carriers as are known in the art to be appropriate.

It will be appreciated by one of ordinary skill in the art that, in addition to the above described pharmaceutical compositions, the sensitizer may be formulated as inclusion complexes, such as cyclodextrin inclusion complexes, or liposomes. Liposomes serve to target the compounds to a particular tissue, such as lymphoid tissue or cancerous hepatic cells. Liposomes can also be used to increase the half-life of the sensitizer. Liposomes useful in the present invention include emulsions, foams, micelles, insoluble monolayers, liquid crystals, phospholipid dispersions, lamellar layers and the like. In these preparations, the active agent to be delivered is incorporated as part of a liposome, alone or in conjunction with a suitable chemotherapeutic agent. Thus, liposomes filled with a desired sensitizer can be directed to the site of a specific tissue type, hepatic cells, for example, where the liposomes then deliver the selected compositions. Liposomes for use in the invention are formed from standard vesicle-forming lipids, which generally include neutral and negatively charged phospholipids and a sterol, such as cholesterol. The selection of lipids is generally guided by consideration of, for example, liposome size and stability of the liposomes in the blood stream. A variety of methods are available for preparing liposomes, as described in, for example, Szoka et al., *Ann. Rev. Biophys. Bioeng.*, 9, 467 (1980), and U.S. Pat. Nos. 4,235,871, 4,501,728, 4,837,028, and 5,019,369. For targeting to the cells of a particular tissue type, a ligand to be incorporated into the liposome can include, for example, antibodies or fragments thereof specific for cell surface determinants of the targeted tissue type. A liposome suspension containing a compound or salt of the present invention may be administered intravenously, locally, topically, etc. in a dose that varies according to the mode of administration, the agent being delivered, and the stage of disease being treated.

"Treating" within the context of the present invention, means an alleviation of symptoms associated with a disorder or disease, or halt of further progression or worsening of those symptoms, or prevention or prophylaxis of the disease or disorder. For example, within the context of treating patients with renal cancer, successful treatment may include a reduction in the proliferation of capillaries feeding the diseased tissue, an alleviation of symptoms related to a cancerous growth or tumor, or a halting in the progression of a disease such as cancer or in the growth of cancerous cells. Treatment may also include administering the pharmaceutical formulations of the present invention in combination with other therapies. For example, the sensitizer and apoptosis-inducing ligand may be administered before, during, or after surgical procedure and/or radiation therapy. The sensitizer and apoptosis-inducing ligand can also be administered in conjunction with other anti-cancer drugs and drugs used in antisense and gene therapy. Appropriate combinations can be determined by those of skill in the oncological and medical arts.

"Preventing" within the context of the present invention, refers to a prophylactic treatment of an individual prone or subject to development of a cancer. For example, those of skill in the oncological and medical arts may be able to determine, based on clinical symptoms and patient history, a statistical predisposition of a particular individual to the development of the cancer. Accordingly, an individual predisposed to the development of a cancer may be treated with a sensitizer and apoptosis-inducing ligand in order to prevent, inhibit, or slow the development of the disease or disorder.

One skilled in the art will appreciate that suitable methods of utilizing a sensitizer and an apoptosis-inducing ligand and administering the sensitizer and an apoptosis-inducing ligand to a human for the treatment or prevention of disease states, in particular, cancers responsive to treatment with apoptosis-inducing ligands (e.g., renal cancers and melanomas) which would be useful in the method of the present invention, are available. Although more than one route can be used to administer the sensitizer and an apoptosis-inducing ligand, a particular route can provide a more immediate and more effective reaction than another route. Accordingly, the described methods are merely exemplary and are in no way limiting.

The dose of the sensitizer and the dose of the apoptosis-inducing ligand administered to a mammal, particularly, a human, in accordance with the present invention should be sufficient to effect the desired response. Such responses include reversal or prevention of the bad effects of the disease for which treatment is desired or to elicit the desired benefit. One skilled in the art will recognize that dosage will depend upon a variety of factors, including the age, condition, and body weight of the human, as well as the source, particular type of the disease, and extent of the disease in the human. The size of the dose of the sensitizer and the dose of the apoptosis-inducing ligand will also be determined by the route, timing and frequency of administration as well as the existence, nature, and extent of any adverse side-effects that might accompany the administration of the dose of the sensitizer and the dose of the apoptosis-inducing ligand and the desired physiological effect. It will be appreciated by one of skill in the art that various conditions or disease states may require prolonged treatment involving multiple administrations.

The term "mammal" includes, but is not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simioids (monkeys) or of the order Anthropoids (humans and apes). An especially preferred mammal is the human. Furthermore, the subject can be the unborn offspring of any of the forgoing hosts, especially mammals (e.g., humans), in which case any screening of the subject or cells of the subject, or administration of compounds to the subject or cells of the subject, can be performed in utero.

Suitable doses and dosage regimens can be determined by conventional range-finding techniques known to those of ordinary skill in the art. Generally, treatment is initiated with smaller dosages that are less than the optimum dose of the sensitizer and/or the apoptosis-inducing ligand. Thereafter, the dosage is increased by small increments until the optimum effect under the circumstances is reached. The present inventive method typically will involve the administration of about 0.01 to about 10 mg, in certain embodiments about 0.1 mg to about 5 mg, and in other embodiments 0.1 mg to about 2 mg, of one or more of the sensitizers and about 0.1 to about 300 mg of the apoptosis inducing ligand described above, per kg body weight of the mammal.

In any of the embodiments of the invention, the cancer can be any cancer in any organ, for example, a cancer is selected from the group consisting of glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, skin carcinoma, melanoma, basal cell carcinoma, squamous cell carcinoma, anaplastic large-cell lymphoma, multiple myeloma, leukemia, lymphoma, cervical carcinoma, and mesothelioma, and combinations thereof. The cancer can be any suitable cancer, for example, follicular thyroid carcinoma, colorectal cancer, pancreatic cancer, leukemias, such as myeloid leukemia, prostate cancer, hepatic cancer, hepatocellular carcinoma, cholangiocarcinoma, cervical and ovarian cancer, cancers of glial origin and renal cancer. As is known in the art, carcinoma generally is a term for cancers that originate in epithelial tissues. Sarcomas originate in mesenchymal tissues and leukemias and lymphomas are blood cancers. As used herein, cancers include carcinomas, sarcomas and leukemias/lymphomas.

In accordance with an embodiment, the methods can be applied to treat patients who are immune compromised, e.g., those who have a reduced p53 function.

In certain embodiments, the invention provides a method of treating prostate cancer in a mammal in need thereof, comprising administering to the mammal an effective amount of a compound of (I):

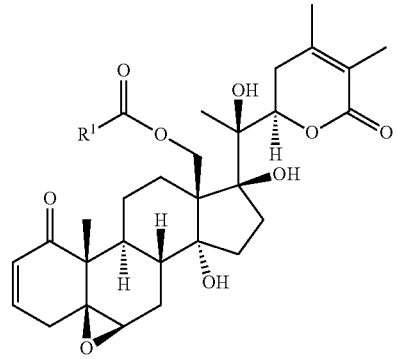

wherein $R^1$ is $C_2$-$C_{10}$ alkyl, $C_3$-$C_8$ cycloalkyl, $C_6$-$C_{10}$ aryl, $C_6$-$C_{10}$ aryl-$C_1$-$C_{10}$ alkyl, $C_6$-$C_{10}$ aryl-$C_2$-$C_{10}$ alkenyl, monocyclic heteroaryl, bicyclic heteroaryl, monocyclic heteroaryl-$C_1$-$C_{10}$ alkyl, bicyclic heteroaryl-$C_1$-$C_{10}$ alkyl, or 4-alkylenyl-tetrahydro-1H-thieno[3,4-d]imidazol-2(3H)-one, wherein the aryl or heteroaryl portion of $R^1$ is optionally substituted with one or more substituents selected from the group consisting of alkyl, alkoxy, aryl, thioalkoxy, heterocyclyl, and nitro, wherein $R^1$ is as described herein, or a compound selected from the group consisting of:

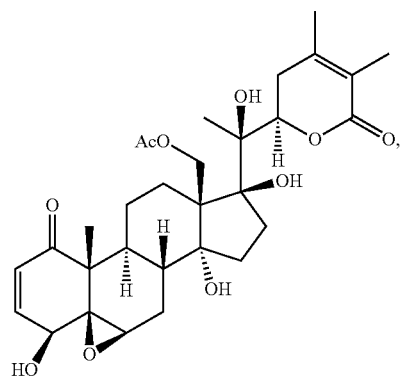

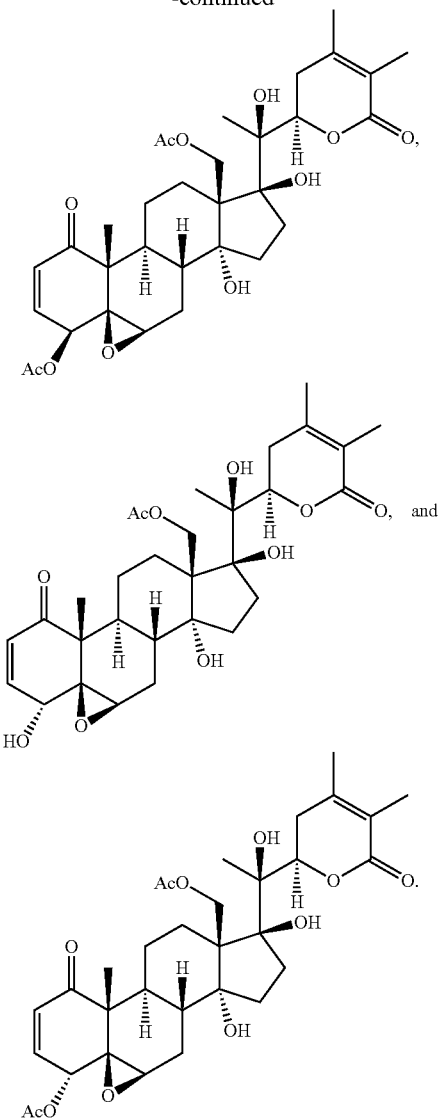

It has been found that the compounds of the invention inhibit prostate cancer cell proliferation. The inventive compounds reduce levels of cFLIP in prostate cancer cells, and the reduction of cFLIP is believed to be involved in the inhibition of prostate cancer proliferation, in both androgen-dependent and castrate-resistant cancer cell lines.

The following examples further illustrate the invention but, of course, should not be construed as in any way limiting its scope.

Example 1

This example demonstrates the extraction and isolation of withanolides from five-month old aeroponically cultivated *P. crassifolia*.

Dried powdered aerial parts of *P. crassifolia* (1.0 kg) were extracted (×3) for 24 h each time with MeOH (1400 mL, 800 mL, and 800 mL) in a shaker at 25° C. and filtered. Resulting filtrates were combined and concentrated in vacuo to afford the crude extract (150.0 g). A portion (50.0 g) of this extract was subjected to solvent-solvent partitioning using 80% aq. MeOH (200 mL) and hexanes (3×100 mL). The resulting 80% aq. MeOH fraction was diluted with water to 50% aq. MeOH and extracted with $CHCl_3$ (3×100 mL). Combined $CHCl_3$ extracts were concentrated under reduced pressure to afford the $CHCl_3$ fraction (5.47 g). This fraction was subjected to column chromatography on RP C (100 g) and eluted with 200 mL each of 60%, 70%, 80%, 90% aq. MeOH and finally with MeOH to afford five fractions A-E: A (698.0 mg) eluted with 60% aq. MeOH; B (608.0 mg) with 70% aq. MeOH; C (522.0 mg) with 80% aq. MeOH; D (1.63 g) with 90% aq. MeOH; and E (2.18 g) with MeOH. Further purification of fraction A (500.0 mg) by RP HPLC using a gradient solvent system (increasing MeOH concentration from 35% aq. MeOH to 60% aq. MeOH in 40 min) afforded sub-fractions $A_1$ and $A_2$. Sub-fraction $A_1$ (72.8 mg) collected at $t_R$=15.4 min was separated by column chromatography over silica gel (10.0 g) and eluted with $CHCl_3$-MeOH (8:2) to afford 15α-acetoxyphysachenolide C (16.9 mg) and 15α-acetoxy-2,3-dihydrophysachenolide D-3β-O-sulfate (35.6 mg). Further purification of sub-fraction $A_2$ (26.9 mg) collected at $t_R$=40.0 min by silica gel (25.0 g) column chromatography and elution with $CHCl_3$-MeOH (85:15) afforded 15α-acetoxy-28-O-β-D-glucopyranosyl-physachenolide D (9.3 mg) and 2,3-dihydrophysachenolide D-3β-O-sulfate (6.6 mg). Fraction B (608.0 mg) obtained above was subjected to further purification by RP HPLC using a gradient solvent system (increasing methanol concentration from 45% aq. MeOH to 70% aq. MeOH in 50 min) yielding eight sub-fractions $B_1$-B8 with retention times ($t_R$s) of 20, 25, 27, 33, 35, 37, 40, and 42 min, respectively. TLC analysis of these indicated that only sub-fractions $B_5$-$B_8$ contained withanolides. Further purification of sub-fraction $B_5$ (53.5 mg) by column chromatography over silica gel (20 g) and elution with $CHCl_3$-MeOH (96:4) afforded 15α-acetoxy-27-O-β-D-glucopyranosylphysachenolide D (24.8 mg). Similar purification of sub-fraction $B_6$ (133.3 mg) gave 15α-acetoxy-28-hydroxyphysachenolide D (124.0 mg). Sub-fraction $B_7$ (32.2 mg) on further purification by silica gel (5.0 g) column chromatography and elution with $CHCl_3$-MeOH (95:5) afforded 27-hydroxyphysachenolide D (9.0 mg). Sub-fraction $B_8$ (24.1 mg) on silica gel (20.0 g) column chromatography and elution with $CHCl_3$-MeOH (96:4) gave 15α,18-diacetoxy-28-hydroxy-17-epi-withanolide K (4.8 mg) and physachenolide C (1) (2.4 mg). Fraction C (522.0 mg) resulting from the first column chromatographic separation was subjected to gel filtration chromatography on Sephadex LH-20 (100.0 g) and eluted with $CH_2Cl_2$-hexanes (4:1). Fractions obtained were combined based on their TLC profiles to afford four sub-fractions $C_1$-$C_4$. TLC investigation of these indicated that only $C_2$ and $C_3$ contained withanolides. Sub-fraction $C_2$ (272.7 mg) on further purification by silica gel NP HPLC [$CHCl_3$-MeOH (95:5), 3 mL/min, UV detection at 254 nm) afforded 15α-acetoxyphysachenolide D (95.0 mg, $t_R$=6.5 min) and physachenolide D (105.0 mg, $t_R$=7.5 min). Sub-fraction $C_3$ (28.2 mg) on further purification by RP HPLC (65% aq. MeOH, 3.0 mL/min, UV detection at 230 nm) gave another portion of physachenolide D (15.5 mg, $t_R$=24.6 min).

Physachenolide C (1)

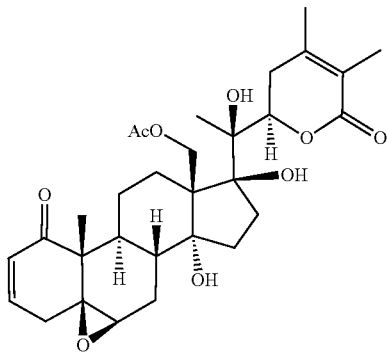

Off-white amorphous powder; $[\alpha]_D^{25}$+102 (c 0.10, MeOH); $^1$H NMR (CDCl$_3$, 400 MHz): δ 6.68 (1H, ddd, J=10.0, 4.8, 2.0 Hz, H-3), 5.91 (1H, dd, J=10.0, 2.0 Hz, H-2), 4.88 (1H, dd, J=9.2, 7.6 Hz, H-22), 4.40 (1H, d, J=11.6 Hz, H-18), 4.30 (1H, d, J=11.6 Hz, H-18), 3.47 (1H, s, H-6α), 3.02-3.12 (2H, m, H-4 and H-23), 2.08 (3H, s, 18-OAc), 1.92 (3H, s, H-28), 1.88 (3H, s, H-27), 1.40 (3H, s, H-21), 1.32 (3H, s, H-19). $^{13}$C NMR (CDCl$_3$, 100 MHz): δ 202.5 (qC, C-1), 170.2 (qC, 18-OAc), 165.5 (qC, C-26), 149.9 (qC, C-24), 142.3 (CH, C-3), 128.9 (CH, C-2), 121.9 (qC, C-25), 88.1 (qC, C-17), 80.9 (qC, C-14), 79.5 (CH, C-22), 78.9 (qC, C-20), 65.3 (CH$_2$, C-18), 64.3 (qC, C-5), 58.7 (CH, C-6), 57.4 (qC, C-13), 48.5 (qC, C-10), 37.9 (CH$_2$, C-16), 35.3 (CH$_2$, C-9), 33.9 (CH$_2$, C-23), 33.8 (CH$_2$, C-4), 32.8 (CH$_2$, C-15), 31.8 (CH, C-8), 25.9 (CH$_2$, C-12), 23.6 (CH$_2$, C-7), 22.1 (CH$_2$, C-11), 21.3 (CH$_3$, 18-OAc), 20.6 (CH$_3$, C-28), 19.4 (CH$_3$, C-21), 15.3 (CH$_3$, C-19), 12.4 (CH$_3$, C-27); LR-APCIMS (positive): m/z 527 [MH]$^+$.

Example 2

This example demonstrates the results of titration experiments on the sensitization of human renal carcinoma cell line ACHN by compounds 1-4 in the presence or absence of TRAIL.

For titration experiments in the presence or absence of TRAIL, ACHN cells were treated with various doses of compounds 1-4 (0.97 nM-500 nM) for 3 or 24 h followed by 10 ng/ml of recombinant TRAIL for 24 h. Cell viability was assessed by addition of MTS during the last four hours of TRAIL treatment. The results are depicted in FIGS. 2A-2D, respectively.

As is apparent from the results depicted in FIGS. 2A-2D, exemplary compounds of the invention (compound 2-4) are superior to the natural product compound 1 for TRAIL apoptosis sensitization.

Example 3

This example the effect of compounds 1 and 3 on the reduction of cFLIP in ACHN human carcinoma cells as a function of concentration after 24 exposure to the compounds.

ACHN human renal carcinoma cells were treated with 125 nM, 250 nM, and 500 nM of compounds 1 and 3. After 24 h exposure to the compounds, Western blotting was performed to separate FLIP$_L$ and FLIP$_S$, and the results shown in FIG. 3.

As is apparent from the results shown in FIG. 3, compound 3 exhibits elevated activity over compound 1 for cFLIP reduction in ACHN renal carcinoma cells.

Example 4

This example demonstrates the effect of various siRNAs on the sensitization of ACHN human renal carcinoma cells to TRAIL apoptosis.

ACHN human renal carcinoma cells were treated with media, siCont, siFLIP smartpool, siFLIP-total, siFLIP-short, and siFLIP-long, in the presence and absence of TRAIL. The percentage decrease in cell number was determined for each experiment, and the results shown in FIG. 4. The inset in FIG. 4 shows Western blotting for cFLIP$_L$ and cFLIP$_S$ for each of the treatments.

As is apparent from the results shown in FIG. 4, specific reduction of cFLIP using siRNA is sufficient for TRAIL apoptosis sensitization. The reduction of both cFLIP$_L$ and cFLIP$_S$ can contribute to TRAIL sensitization.

Example 5

This example demonstrates the results of titration experiments on the sensitization of SK-MEL-28 melanoma cell line by compounds 1-4 in the presence or absence of poly (I:C).

For titration experiments in the presence or absence of TRAIL, ACHN cells were treated with various doses of compounds 1-4 (0.97 nM-500 nM) for 3 or 24 h followed by 10 ng/ml of poly (I:C) for 24 h. Cell viability was assessed by addition of MTS during the last four hours of poly (I:C). The results are depicted in FIGS. 5A-5D, respectively.

As is apparent from the results depicted in FIGS. 5A-5D that exemplary compounds of the invention (compound 2-4) are superior to the natural product compound 1 for poly (I:C) apoptosis sensitization.

Example 6

This example demonstrates the effect of compound 1 and 3 on the reduction of cFLIP$_L$, cFLIP$_S$, and GAPDH in M14 human melanoma cells as a function of concentration.

M14 human melanoma cells were treated with 0, 31.25, 62.5, 125, 250, or 500 nM of compounds 1 and 3. After 24 h, Western blotting was performed to separate cFLIP$_L$, cFLIP$_S$, and GAPDH. The results are shown in FIG. 6.

As is apparent from the results depicted in FIG. 6, compound 3 exhibits elevated activity over compound 1 for cFLIP reduction in M14 melanoma cells.

Example 7

This example demonstrates the effect of several cFLIP siRNAs on the sensitization of SK-MEL-28 melanoma cells to poly (I:C)-mediated apoptosis.

SK-MEL-28 melanoma cells were treated with media, siRNA control, and siRNA cFLIP smart pool in the presence or absence of poly (I:C). The percentage decrease in cell number was determined, and the results shown graphically in FIG. 7A. The insert for FIG. 7A shows a Western blot of FLIP$_L$ and FLIP$_S$ for cells treated with siRNA control and siRNA cFLIP.

SK-MEL-28 melanoma cells were treated with media, siRNA control, siRNA cFLIP smart pool, siRNA cFLIP short, siRNA cFLIP long, and si RNA cFLIP total in the presence or absence of poly (I:C). The percentage decrease in cell number was determined, and the results shown graphically in FIG. 7B.

As is apparent from the results depicted in FIGS. 7A and 7B, reduction of both cFLIP$_L$ and cFLIP$_S$ can contribute to poly (I:C) sensitization.

Example 8

This example demonstrates a comparison of the sensitization of human renal cancer lines to TRAIL apoptosis in ACHN, SN12C, Caki-2, TK-10, and UO-31 renal carcinoma cells exhibited by compound 1, the IAP antagonists Birinapant, GDC-0152, and LCL-161 and the Bcl-2 antagonists ABT-199 and ABT-737.

ACHN, SN12C, Caki-2, TK-10, and UO-31 cells were treated with compound 1, the IAP antagonists Birinapant, GDC-0152, or LCL-161 and the Bcl-2 antagonists ABT-199 and ABT-737 in the presence and absence of TRAIL. The percentage decrease in cell numbers were determined, and the results shown in FIGS. 8A-8C.

As is apparent from the results depicted in FIGS. 8A-8C, compound 1 exhibited superior results in sensitization of TRAIL apoptosis in the 5 renal carcinomas compared to the IAP antagonists Birinapant, GDC-0152, or LCL-161 and the Bcl-2 antagonists ABT-199 and ABT-737.

Example 9

This example demonstrates a comparison of the sensitization of human renal cancer lines to TRAIL apoptosis in 888, 1383, and Baldwin renal melanoma cells exhibited by compounds 1 and 3, the IAP antagonist Birinapant and the Bcl-2 antagonist ABT-737.

888, 1383, and Baldwin renal melanoma cells were treated with compound 1 of compound 3, the Birinapant, or ABT-737 in the presence and absence of TRAIL. The percentage decrease in cell numbers were determined, and the results shown in FIGS. 8A-8C.

As is apparent from the results shown in FIGS. 8A-8C, compounds 1 and 3 exhibited superior results in sensitization of TRAIL apoptosis in the 5 renal melanomas compared to Birinapant or ABT-737.

Example 10

This example demonstrates the results of a human M14 melanoma xenograft model in athymic nude mice.

Athymic nude mice were injected with 1×10$^6$ human melanoma cells s.c. Tumors were allowed to grow 4-5 weeks and then vehicle or compound 1, poly (I:C), or compound 1+poly (I:C) were injected intra-tumor. Tumor growth was monitored until endpoint. Tumor volume was measured over 7 weeks after the first treatment, and the results shown in FIG. 10A.

TUNEL staining for apoptosis in M14 cells was performed at 24 h after the second injection, and the results shown in FIG. 10B.

As is apparent from the results shown in FIG. 10A, tumor volume was the lowest in mice treated with compound 1+poly (I:C) after 7 weeks. The percent apoptosis positive cells were the highest in mice treated with compound 1+poly (I:C).

Example 11

This example demonstrates the results of B16F10 melanoma xenograft model in C57B/6 mice.

C57B/6 mice were injected with 5×10$^5$ B16F10 melanoma cells s.c. Tumors were allowed to grow 8-10 days and then vehicle, compound 1, or compound 3 were injected intra-tumor twice a week for 3 weeks. Tumor growth was monitored until endpoint. Tumor volume was measured over 8 weeks after the first treatment, and the results shown in FIG. 11.

As is apparent from the results shown in FIG. 11, tumor volume was lowest in mice treated with compound 3.

Example 12

This example demonstrates the effect on cell number of SK-MEL-28 melanoma cells treated with media, compound 1, or compound 1+α-TNFα and then incubated with activated human T cells.

Activated Human T Effector Cells.

6 well costar plates were precoated with anti-CD3 (1 ug/ml) in PBS overnight at 4° C. Wells were washed with PBS then blocked with RPMI+10% FBS for 30 min before adding anti-CD28 (0.2 ug/ml) and purified T cells.

T cells were isolated from human PBMCs using Pan T cell isolation kit (Miltenyi Biotech) as per manufacturers protocol, added to the costar plates and incubated at 37° C. 24 hours later activated T cells were used as effectors.

Melanoma Target Cells.

SK-MEL-28 cells (200,000) were added to costar 6 plates. After 24 h PCC (500 nM) or control DMSO was added, followed 24 h later by addition of activated T cells at different target to effector ratios. After a further 24 hours plates were washed and adherent melanoma cells were fixed with methanol and stained with crystal violet.

SK-MEL-28 melanoma cells were treated with media, compound 1, or compound 1+α-TNFα and then incubated with the activated human T cells. The percentage reduction in cell number was determined and the results shown in FIG. 12.

As is apparent from the results shown in FIG. 12, compound 1 enhanced the killing of human melanoma cells by activated T cells. Neutralizing antibodies to TNFα partially blocked the T cell killing of the melanoma cells.

Example 13

This example demonstrates selective growth inhibition (IC$_{50}$, nM) of prostate cancer cells by compounds of the invention, in accordance with an embodiment.

LNCaP and 22Rv1 prostate cancer cells and human fibroblasts HFF cells were treated with compounds 1, 2, 3, and 4. The growth inhibition is set forth in Table 1

TABLE 1

| Compound | LNCaP | 22Rv1 | HFF |
|---|---|---|---|
| 1 | 37 ± 2 | 48 ± 2 | >2000 |
| 2 | 18 ± 2 | 16 ± 4 | 938 ± 10 |
| 3 | 14 ± 1 | 10 ± 2 | 892 ± 119 |
| 4 | 17 ± 8 | 17 ± 1 | 945 ± 92 |

As is apparent from the results set forth in Table 1, growth inhibitor activity of compounds 1-4 was much greater for prostate cancer cells than other cells tested.

Example 14

This example demonstrates the effect on cFLIP levels of compounds 1 and 3 in LNCaP prostate cancer cells.

LNCaP prostate cancer cells were treated with 125 nM, 250 nM, or 500 nM of compounds 1 or 3. A Western blot was obtained and is shown in FIG. 13.

As is apparent from FIG. 13, treatment of LNCaP cells with compounds 1 and 3 resulted in reduction of cFLIP levels.

Example 15

This example demonstrates the effect on cFLIP levels of compounds 1 and 3 in 22Rv1 prostate cancer cells.

22Rv1 prostate cancer cells were treated with 125 nM, 250 nM, or 500 nM of compounds 1 or 3. A Western blot was obtained and is shown in FIG. 13.

As is apparent from FIG. 14, treatment of 22Rv1 cells with compounds 1 and 3 resulted in reduction of cFLIP levels.

Example 16

This example demonstrates the effect of physachenolide C (PCC) on tumor volume of tumors originating from M14 human melanoma cells injected into immunodeficient NSG mice.

The structure of physachenolide C (PCC) is shown in FIG. 16.

Immunodeficient NSG mice injected with $1\times10^6$ M14 human melanoma cells. When tumors were 75-100 mm$^3$ (day 0), mice were injected with $5\times10^6$ peripheral blood mononuclear cells (PBLSs) or saline (i.v.). Two weeks later mice were treated with 10 mg/kg PCC or vehicle control (DMSO+Trappsol) (i.t.) twice weekly for 3 weeks. Tumor growth was monitored until end point (day 50). The data is shown in FIG. 18 and is representative of three separate experiments. ** $p<0.0001$ and  $p<0.0089$.

Example 17

This example demonstrates identification of major cellular proteins interacting with PCC.

Biotinylated PCC (LG161) was bound to Streptavidin beads and incubated with M14 cell extracts followed by washing and elution of bound proteins. PCC was first added to some of the M14 extracts to compete for specific binding sites. Elutants were then subjected to gel electrophoresis and analyzed by SDS PAGE as shown in FIG. 19A. Mass spectrometry analysis of excised gel bands is shown in FIG. 19B. Western blotting is shown in FIG. 19C.

As is apparent for the results shown in FIG. 19C, BRD2, BRD3, and BRD4 are present in the M14 cell extracts.

Example 18

This example demonstrates the effect of siRNA on bromodomain (BRD) proteins on apoptosis induced by TRAIL or poly(I:C).

ACHN (5000 cells per well) were plated in a 96 well plate for 24 hours in RPMI complete medium and treated with 50 nM siRNA (siRNA against BRD2, BRD3, BRD4, and cFLIP) (smart pools, Dharmacon) in Lipofectamine RNAiMAX diluted with OptiMEM according to the manufacturer's protocol (Invitrogen). For M14 or SK-MEL-28 cells (5000 per well) reverse transfection method was adopted where cells were treated with 50 nM siRNA (diluted as above) and then plated for 48 hours in DMEM complete medium. 48 hours after siRNA transfection, ACHN cells were treated with media or 50 ng/ml of TRAIL and M14 and SK-MEL28 cells were treated with media or 10 ug/ml poly (I:C) for 24 hours. Viable cell number was determined using an MTS assay (Promega). Reduction in viable cell number vs. the media control is plotted in FIG. 20A for ACHN cells, FIG. 20B for M4 cells, and FIG. 20C for SK-MEL-28 cells. * $p<9.6E-06$ and  $p<0.003$ and * $p<0.016$ (ACHN), ** $p<0.0015$ and * $p<0.003$ (M14) and ** $p<8.61E-06$ and * $p<0.0045$ (SK-MEL-28) cells.

As is apparent from the results shown in FIGS. 20A and 20B, for apoptosis sensitization, BRD4 is most important for melanoma cells (M14). For apoptosis sensitization in renal carcinoma cells (ACHN), both BRD2 and BRD4 may be involved.

Example 19

This example demonstrates the effect of transfection of prostate cancer cell lines LNCaP, LNCaP 95, VCaP, and 22Rv2 with the siRNAs siBrd2, siBrd3, siBrd4, and siFLIP on the percentage decrease in cell number.

Prostate cancer cell lines were plated in 96 well plates at 5,000 cells/well and incubated overnight. The following day the cells were transfected with 50 nM siRNA (smart pools, Dharmacon) in Lipofectamine RNAiMAX diluted with OptiMEM according to the manufacturer's protocol (Invitrogen). Plates were incubated for 6 days and then viable cell number was determined using an MTS assay (Promega). Reduction in viable cell number vs. the media control is shown in FIG. 21.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula (I):

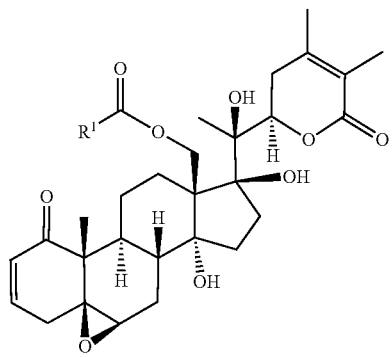

wherein $R^1$ is $C_3$-$C_{10}$ alkyl, $C_3$-$C_8$ cycloalkyl, $C_6$-$C_{10}$ aryl, $C_6$-$C_{10}$ aryl-$C_1$-$C_{10}$ alkyl, $C_6$-$C_{10}$ aryl-$C_2$-$C_{10}$ alkenyl, monocyclic heteroaryl, bicyclic heteroaryl, monocyclic heteroaryl-$C_1$-$C_{10}$ alkyl, bicyclic heteroaryl-$C_1$-$C_{10}$ alkyl, or 4-alkylenyl-tetrahydro-1H-thieno[3,4-d]imidazol-2(3H)-one, wherein the aryl or heteroaryl portion of $R^1$ is optionally substituted with one or more substituents selected from the group consisting of alkyl, alkoxy, aryl, thioalkoxy, heterocyclyl, and nitro.

2. The compound of claim 1, wherein $R^1$ is $C_3$-$C_8$ cycloalkyl, $C_6$-$C_{10}$ aryl, $C_6$-$C_{10}$ aryl-$C_1$-$C_{10}$ alkyl, $C_6$-$C_{10}$ aryl-$C_2$-$C_{10}$ alkenyl, monocyclic heteroaryl, bicyclic heteroaryl, monocyclic heteroaryl-$C_1$-$C_{10}$ alkyl, bicyclic heteroaryl-$C_1$-$C_{10}$ alkyl, or 4-alkylenyl-tetrahydro-1H-thieno[3,4-d]imidazol-2(3H)-one, wherein the aryl or heteroaryl portion of $R^1$ is optionally substituted with one or more substituents selected from the group consisting of alkyl, alkoxy, aryl, thioalkoxy, heterocyclyl, and nitro.

3. The compound of claim 2, wherein $R^1$ is

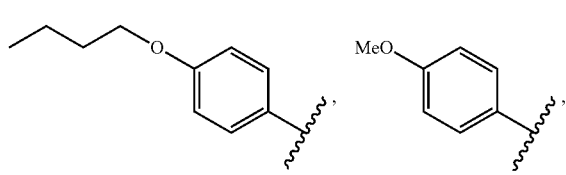

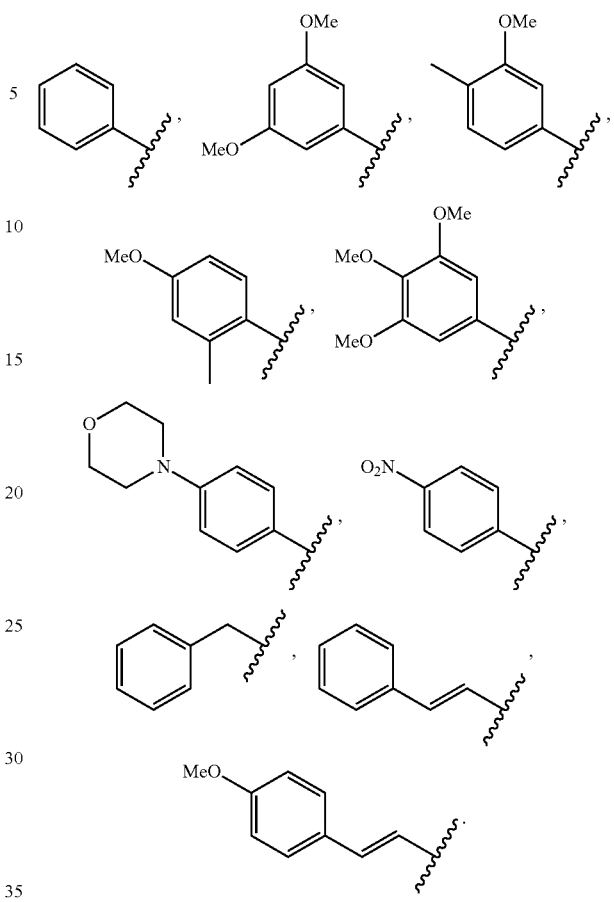

4. The compound of claim 2, wherein $R^1$ is

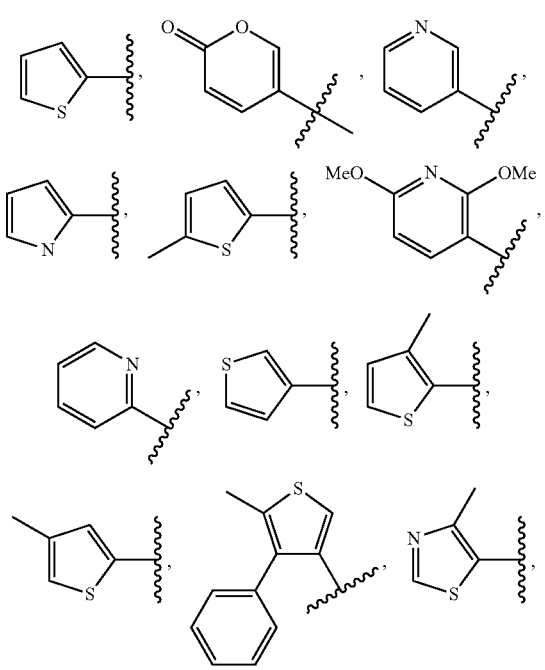

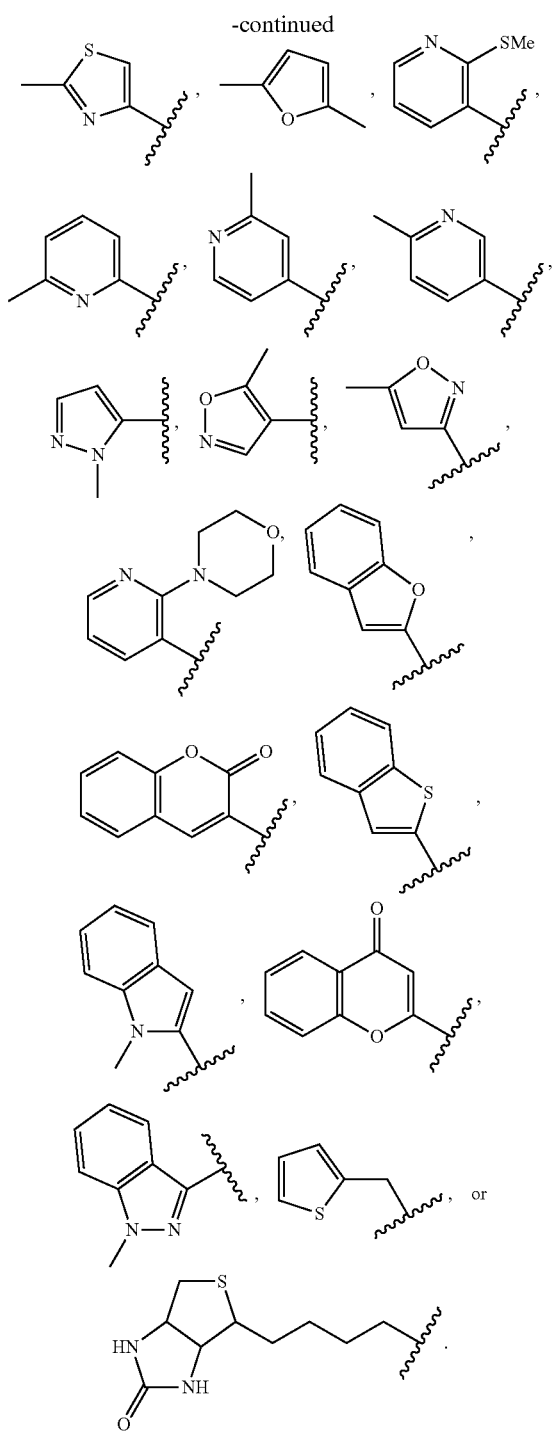

6. A pharmaceutical composition comprising a compound of claim 2 and a pharmaceutically acceptable carrier.

7. A pharmaceutical composition comprising a compound of claim 3 and a pharmaceutically acceptable carrier.

8. A pharmaceutical composition comprising a compound of claim 4 and a pharmaceutically acceptable carrier.

9. The compound of claim 2, which is selected from the group consisting of

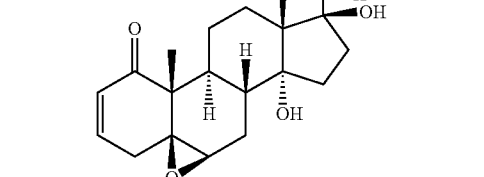

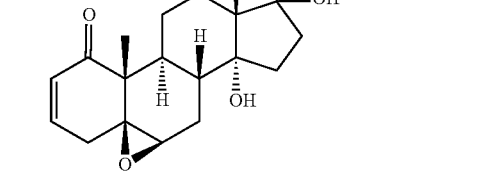

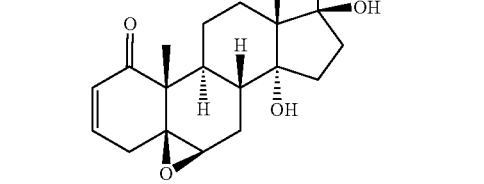

5. A pharmaceutical composition comprising the compound of claim 1 and a pharmaceutically acceptable carrier.

10. A pharmaceutical composition comprising a compound of claim 9 and a pharmaceutically acceptable carrier.

* * * * *